United States Patent
Dell et al.

(10) Patent No.: US 9,835,591 B2
(45) Date of Patent: Dec. 5, 2017

(54) OPTICAL CANTILEVER BASED ANALYSIS

(71) Applicant: University of Western Australia, Perth, Western Australia (AU)

(72) Inventors: John Marcel Dell, Bull Creek (AU); Mariusz Martyniuk, Wattle Grove (AU); Adrian John Keating, Mt. Hawthorn (AU); Gino Michael Putrino, Dianella (AU); Lorenzo Faraone, Mt. Lawley (AU); Dilusha Silva, Ballajura (AU); Roger Jeffery, Balcatta (AU)

(73) Assignee: PANORAMA SYNERGY LTD, Melbourne, Victoria (AU)

( * ) Notice: Subject to any disclaimer, the term of this patent is extended or adjusted under 35 U.S.C. 154(b) by 0 days.

(21) Appl. No.: 14/473,807

(22) Filed: Aug. 29, 2014

(65) Prior Publication Data

US 2014/0368829 A1 Dec. 18, 2014

Related U.S. Application Data

(63) Continuation-in-part of application No. 14/144,290, filed on Dec. 30, 2013, now Pat. No. 9,057,706, (Continued)

(30) Foreign Application Priority Data

Feb. 7, 2012 (AU) ................ 2012900444

(51) Int. Cl.
*G01B 9/02* (2006.01)
*G01N 29/02* (2006.01)
(Continued)

(52) U.S. Cl.
CPC ....... *G01N 29/022* (2013.01); *G01N 21/7746* (2013.01); *G01N 29/036* (2013.01); (Continued)

(58) Field of Classification Search
CPC G01J 3/02; G01J 3/26; H01L 31/0232; H01L 31/1032; G01G 3/165; G01N 21/17; (Continued)

(56) References Cited

U.S. PATENT DOCUMENTS 5,260,567 A 11/1993 Kuroda et al.
5,260,926 A 11/1993 Kuroda et al.
(Continued)

FOREIGN PATENT DOCUMENTS

WO 2004/112050 A1 12/2004
WO 2006/138697 A2 12/2006
WO 2007/121208 A2 10/2007

OTHER PUBLICATIONS

Final Office Action dated Mar. 12, 2015 for U.S. Appl. No. 13/761,987.
(Continued)

*Primary Examiner* — Sunghee Y Gray
(74) *Attorney, Agent, or Firm* — Howard & Howard Attorneys PLLC

(57) ABSTRACT

An optical sensor including a MEMS structure, and a grating coupled resonating structure positioned adjacent to the MEMS structure, the grating coupled resonating structure comprising an interrogating grating coupler configured to direct light towards the MEMS structure. The interrogating grating coupler is two dimensional, and the interrogating grating coupler and the MEMS structure form an optical resonant cavity.

20 Claims, 15 Drawing Sheets

Related U.S. Application Data which is a continuation-in-part of application No. 13/035,374, filed on Feb. 25, 2011, now Pat. No. 8,649,018, which is a continuation of application No. 13/761,987, filed on Feb. 7, 2013, now abandoned.

(51) Int. Cl.

| | | |
|---|---|---|
| *G01N 21/77* | (2006.01) | |
| *G01N 29/036* | (2006.01) | |
| *G01N 29/24* | (2006.01) | |
| *G02B 26/08* | (2006.01) | |
| *G01Q 20/02* | (2010.01) | |
| *B82Y 20/00* | (2011.01) | |

(52) U.S. Cl.
CPC ..... *G01N 29/2418* (2013.01); *G02B 26/0833* (2013.01); *B82Y 20/00* (2013.01); *G01N 2201/08* (2013.01); *G01N 2291/0255* (2013.01); *G01N 2291/0256* (2013.01); *G01N 2291/0427* (2013.01); *G01Q 20/02* (2013.01)

(58) Field of Classification Search
CPC ... G01N 2291/0256; G01N 2291/0427; G01N 33/54373; G01B 9/02004; G02B 6/3566
USPC ....................................................... 356/480
See application file for complete search history.

(56) References Cited

U.S. PATENT DOCUMENTS

| | | | |
|---|---|---|---|
| 5,274,230 A | 12/1993 | Kajimura et al. | |
| 5,465,611 A | 11/1995 | Ruf et al. | |
| 5,540,958 A | 7/1996 | Bothra et al. | |
| 6,577,417 B1 | 6/2003 | Khoury | |
| 6,591,658 B1 | 7/2003 | Yedur et al. | |
| 6,987,898 B2 | 1/2006 | Tran et al. | |
| 7,319,527 B2* | 1/2008 | Frederix ............... | B82Y 35/00 356/501 |
| 7,339,738 B1* | 3/2008 | Carr .................... | G02B 26/0808 359/291 |
| 7,518,737 B2* | 4/2009 | Hall ....................... | G01D 5/266 356/498 |
| 7,671,511 B2 | 3/2010 | Battiston | |
| 7,797,757 B2 | 9/2010 | Degertekin | |
| 7,872,759 B2 | 1/2011 | Tearney et al. | |
| 2002/0039463 A1 | 4/2002 | Degertekin et al. | |
| 2002/0057757 A1 | 5/2002 | Khoury | |
| 2003/0167830 A1 | 9/2003 | Buguin et al. | |
| 2003/0227632 A1 | 12/2003 | Marcus et al. | |
| 2004/0062550 A1 | 4/2004 | Terahara et al. | |
| 2004/0076008 A1 | 4/2004 | Ikeda | |
| 2006/0098928 A1 | 5/2006 | Koch et al. | |
| 2006/0194346 A1 | 8/2006 | Knoll et al. | |
| 2006/0213259 A1 | 9/2006 | Prinz et al. | |
| 2006/0283338 A1 | 12/2006 | Degertekin | |
| 2007/0012094 A1 | 1/2007 | Degertekin et al. | |
| 2007/0054339 A1 | 3/2007 | Lin et al. | |
| 2007/0089496 A1 | 4/2007 | Degertekin | |
| 2007/0093971 A1 | 4/2007 | Candy et al. | |
| 2007/0103697 A1 | 5/2007 | Degertekin | |
| 2007/0107501 A1 | 5/2007 | Taber | |
| 2007/0195333 A1 | 8/2007 | Negishi | |
| 2007/0295064 A1 | 12/2007 | Degertekin et al. | |
| 2008/0061230 A1 | 3/2008 | Wang et al. | |
| 2008/0168830 A1 | 7/2008 | Degertekin | |
| 2008/0193133 A1* | 8/2008 | Krug ................. | G02B 6/12007 398/83 |
| 2008/0253728 A1 | 10/2008 | Sparacin et al. | |
| 2009/0002714 A1 | 1/2009 | Iannuzzi et al. | |
| 2009/0051924 A1 | 2/2009 | Ito et al. | |
| 2010/0149545 A1* | 6/2010 | Aeppli ................. | G01B 11/165 356/501 |
| 2010/0218288 A1 | 8/2010 | Sarioglu et al. | |
| 2010/0238454 A1 | 9/2010 | Pruessner et al. | |
| 2011/0304854 A1 | 12/2011 | Li | |
| 2012/0218559 A1 | 8/2012 | Dell et al. | |

OTHER PUBLICATIONS

Lavrik et al., "Cantilever transducers as a platform for chemical and biological sensors", Rev. Sci. Instrum., Jul. 2004, pp. 2229-2253, vol. 74, No. 7, AIP Publishing LLC.

Committee on Assessment of Security Technologies for Transportation, National Research Council, "Opportunities to Improve Airport Passenger Screening with Mass Spectrometry", The National Academies Press, 2004, 56 pages, Washington, DC.

Canas et al., "Mass spectrometry technologies for proteonnics", Briefings in Functional Genomics and Proteomics, Feb. 3, 2006, pp. 295-320, vol. 4, No. 4, Oxford University Press.

Wapelhorst et al., "Complex MEMS: A fully integrated TOF micro mass spectrometer", Sensors and Actuators A, 2007, pp. 22-27, vol. 138, Elsevier B.V.

Loui et al., "Chemical vapor discrimination using a compact and low-power array of piezoresistive microcantilevers", The Analyst (The Royal Society of Chemistry), May 2008, pp. 608-615, vol. 133, No. 5, RSC Publishing.

Baller et al., "A cantilever array-based artificial nose", Ultramicroscopy, 2000, pp. 1-9, vol. 82, Elsevier Science B.V.

Yang et al., "Zeptogram-Scale Nanomechanical Mass Sensing", Nano Letters, Apr. 2006, pp. 583-586, vol. 6, No. 4, The American Chemical Society.

Li et al., "Ultra-sensitive NEMS-based cantilevers for sensing, scanned probe and very high-frequency applications", Nature Nanotechnology, 2007, 3 pages, vol. 2, Issue 2.

Stievater et al., "All-optical micromechanical chemical sensors", Appl. Phys. Lett., 2006, pp. 091125-1-091125-3, vol. 89, AIP Publishing LLC.

Kong et al., "A MEMS Sensor Array for Explosive Particle Detection", Proc. IEEE Int. Conf. Inform., 2004, pp. 278-281.

Hickman et al., "Selective Functionalization of Gold Microstructures with Ferrocenyl Derivatives via Reaction with Thiols or Disulfides: Characterization by Electrochemistry and Auger Electron Spectroscopy", J. Am. Chem. Soc., 1991, pp. 1128-1132, vol. 113, American Chemical Society.

Xu et al., "Optical Polymer Waveguide Based Cantilevers for Chemical and Biological Sensors", IEEE Sensors Conf., 2005, pp. 963-966, IEEE.

Taillaert et al., "Grating Couplers for Coupling between Optical Fibers and Nanophotonic Waveguides", Japanese Journal of Applied Physics, 2006, pp. 6071-6077, vol. 45, No. 8A.

Jalali et al., "Silicon Photonics", Journal of Lightwave Technology, Dec. 2006, pp. 4600-4615, vol. 24, No. 12, IEEE.

Boiadjiev et al., "Photochemical Hydrosilylation of 11-Undecenyltriethylammonium Bromide with Hydrogen-Terminated Si Surfaces for teh Development of Robust Microcantilever Sensors for Cr(VI)", Langmuir—The ACS Journal of Surfaces and Colloids, Feb. 15, 2005, pp. 1139-1142, vol. 21, No. 4, American Chemical Society.

Langer et al., "Controlled Silicon Surface Functionalization by Alkene Hydrosilylation", J. Am. Chem. Soc., 2005, pp. 12798-12799, vol. 127, American Chemical Society.

Hsieh et al., "Limits of Recognition for Simple Vapor Mixtures Determined with a Microsensor Array", Annal. Chem., 2004, pp. 1885-1895, vol. 76, American Chemical Society.

MEEP from AbInitio, printed Aug. 18, 2013—available at ab-initio.mit.edu/wiki/index.php/Meep, pp. 1-3.

See http://www.youtube.com/watch?v=nMByfOrk4Is (Recorded during a University of Western Australia 3-minute thesis competition around Jun.-Aug. 2010).

"Opportunities to Improve Airport Passenger Screening with Mass Spectrometry", The National Academies Press, 2004, pp. 1-5, Washington, DC (www.nap.edu/catalog.php?record_id=10996).

Kauppinen et al., "Grated Waveguide Optical Cavity as a Compact Sensor for Sub-nanometre Cantilever Deflections", Eindhoven, 2008, pp. 111-114, WeF3, The Netherlands.

(56) References Cited

OTHER PUBLICATIONS

Pham et al., "Read-Out of Cantilever Bending With a Grated Waveguide Optical Cavity", IEEE Photonics Technology Letters, Feb. 15, 2011, pp. 215-217, vol. 23, No. 4, IEEE.
Regenauer-Lieb et al., iVEC Research Outcomes, iVEC Annual Report 2009-2010, pp. 1-76, Published Sep. 14, 2010.
Putrino et al., "Comparison of dynamic and static operation of a novel optical read-out technology for micromachined cantilever sensors", The University of Western Australia, 2010, pp. 21-22, IEEE, Crawley, WA, Australia.
Martyniuk et al., "MEMS-based chem- and bio-sensor arrays", The University of Western Australia, Nov. 2010, 14 pages, Microelectronics Research Group.
Putrino et al. (2), "A novel multiplexed optical read-out technology for micromachined cantilever sensor arrays using diffraction gratings", The University of Western Australia, Jul. 6, 2010, 2 pages, Crawley, WA, Australia.
Kirill Zinoviev et al., "A Novel Optical Waveguide Microcantilever Sensor for the Detection of Nanomechanical Forces, Journal of Lightwave Technology", May 2006, pp. 2132-2138, vol. 24, No. 5, Instituto de Microelectronica de Madrid, Madrid 28760, Spain.
International—Type Search Report (Dated Aug. 22, 2012).
Brereton, "Chemometrics: Data Analysis for the Laboratory and Chemical Plant", 2003, University of Bristol, UK, pp. 1-489, John Wiley & Sons Ltd., The Atrium, Southern Gate, Chichester, West Sussex, PO 19 8SQ, England.
See http://www.epixfab.eu/—webpage attached.
Huang et al., "Design and Development of Tunable Filters for MEMS Adaptive Infrared Detectors", Nanotechnology and Precision Engineering, Mar. 2006, pp. 38-45, vol. 4, No. 1.
Huang et al., "Effect of deposition conditions on mechanical properties of low-temperature PECVD silicon nitride films", Materials Science and Engineering A 435-436, 2006, pp. 453-459, Elsevier B.V.
Martyniuk et al., "Dielectric thin films for MEMS-based optical sensors", Microelectronics Reliability, 2007, pp. 733-738, vol. 47, Elsevier Ltd.
Walmsley et al., "Process condition dependence of mechanical and physical properties of silicon nitride thin films", J. Appl. Phys., 2007, pp. 103517-1-103517-6, vol. 102, AIP Publishing LLC.
Martyniuk et al., "Stress in low-temperature plasma enhanced chemical vapour deposited silicon nitride thin films", Smart Materials and Structures, 2006, pp. S29-S38, vol. 15, Institute of Physics Publishing, UK.
Carroll et al., "Optimizing polarization-diversity couplers for Si-photonics: reaching the -1dB coupling efficiency threshold", Optics Express, Jun. 9, 2014, pp. 14769-14781, vol. 22, No. 12.
Advisory Action (U.S. Appl. No. 14/846,570); dated Sep. 29, 2016.
Final Office Action (U.S. Appl. No. 14/846,570); dated Jul. 15, 2016.
Final Office Action (U.S. Appl. No. 14/846,570); dated Mar. 20, 2017.
Non-Final Office Action (U.S. Appl. No. 14/846,570); dated Apr. 3, 2017.

\* cited by examiner

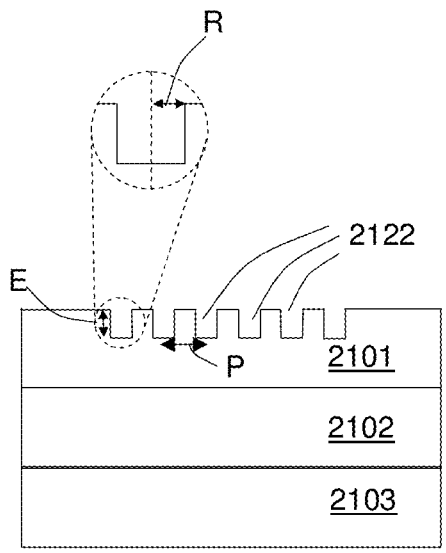
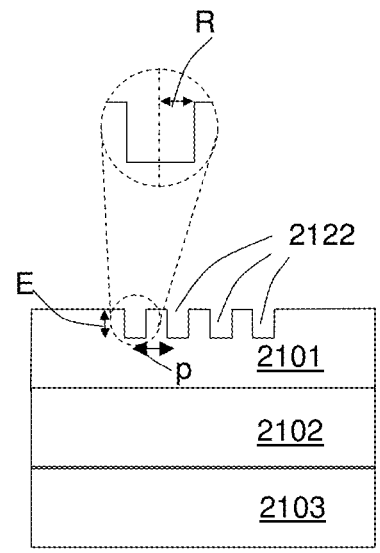
Section A-A of FIG. 15          Section B-B of FIG. 15
FIG. 16          FIG. 17
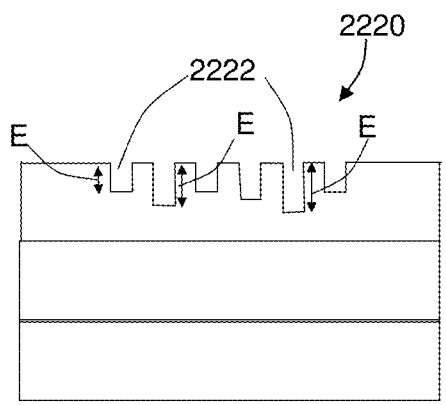
FIG. 18

OPTICAL CANTILEVER BASED ANALYSIS

CROSS REFERENCE TO RELATED APPLICATION

This application is a continuation-in-part of U.S. patent application Ser. No. 14/144,290, filed Dec. 30, 2013, which is a continuation-in-part of U.S. patent application Ser. No. 13/035,374, filed Feb. 25, 2011 (now U.S. Pat. No. 8,649,018, issued Feb. 11, 2014) and U.S. patent application Ser. No. 13/761,987, filed Feb. 7, 2013, which claims priority to Australian Patent Application No. 2012900444, filed Feb. 7, 2012, the disclosures of which are hereby incorporated by reference in their entirety.

FIELD OF THE INVENTION

The present invention relates to an optical sensor and a method for determining a deflection of a beam, a cantilever or any suitable MicroElectroMechanical Systems (MEMS) structure.

BACKGROUND OF THE INVENTION

Different methods for detecting chemical and biological analytes have been used. Such technology has been used, for example, in process control, environmental monitoring, medical diagnostics and security.

Mass spectroscopy is one approach to detect such analytes. The process begins with an ionized sample. The ionized sample is shot through a vacuum that is subjected to an electromagnetic field. The electromagnetic field changes the path of lighter ions more than heavier ions. A series of detectors or a photographic plate are then used to sort the ions depending on their mass. The output of this process, which is the signal from the detectors or the photographic plate, can be used to determine the composition of the analytes in the sample.

A disadvantage of mass spectroscopy instruments is that they are generally high-cost instruments. Additionally, they are difficult to ruggedize, and are not useful for applications that require a sensor head to be remote from signal-processing electronics.

A more recent approach is to use Micro Electro Mechanical Systems (MEMS)-based microstructures, and more specifically micro-cantilevers. These are extremely sensitive systems, and several demonstrations of mass sensors that have detection limits as low $10^{-21}$ g, approximately the mass of a single protein molecule, have been performed. While these experiments have been performed in idealised environments, practical cantilever-based systems have been demonstrated for the detection of a wide range of single analytes.

With these sensors, a portion of the micro-cantilever is coated with an analyte selective coating to which the analyte is adsorbed. There are two common modes of operation of micro-cantilever sensors, namely static and dynamic.

In the static mode, a stress differential is induced across the cantilever due to preferential adsorption of an analyte onto the analyte selective coating causing the cantilever to bend. The extent of the bending is in direct relation to the amount of analyte adsorbed. The stress differential can be induced by the analyte causing swelling of an overlayer, or by changes in the Gibbs free energy of the surface.

In the dynamic mode, the adsorbed analyte changes the mass of the cantilever and hence its mechanical resonance frequency. The rate and size of the change in resonance frequency is then measured to estimate the analyte concentration. Active sensing using these structures is achieved by resonant excitation.

In general, long, compliant cantilevers are required for sensitive static sensors, while high sensitivity for dynamic sensors dictate that short, stiff beams with high Q-factor mechanical resonances are needed. The most sensitive MEMS-based sensors to date have been based on measurements of resonant frequency.

Readout technologies used with micro-cantilever sensors are primarily based on optical techniques developed for atomic force microscopy (AFM) analysis. Here, light is reflected from the cantilever tip to a distant quadrant detector, which process is referred to as optical leveraging. Electrical sensing and optical sensing techniques are also used. Electrical sensing includes piezoresistive, piezoelectric, capacitive, Lorentz force/emf sensing and tunneling current techniques. Optical sensing techniques include optical sensing based on optical interference, the optical interference being either in an interferometer or in the use of diffraction from an optical grating formed by a line of cantilevers. This latter configuration using an optical grating formed by a line of cantilevers is often described as an array in literature, but is still effectively a sensor for a single analyte.

Another approach to analyte detection is where large, compact, integrated arrays of individual sensors are used, particularly for multi-analyte, multi-analysis applications. These are particularly useful when an unknown substance is to be identified or if there is a number of chemical species to be tested for simultaneously. Examples of such requirements can be found in the screening of food for pesticide residues where there are many different potential contaminants, detection of different antibodies in a single blood sample, or the presence of any of the many possible illicit drugs or explosives in luggage. Additionally, an array of sensors can also give significantly improved statistics of detection (including fewer false-positives and false-negatives) by averaging the response over a large number of sensors, and allows the use of multivariate statistical chemometric techniques, as are typically applied in spectroscopic analysis.

There are several disadvantages with the sensors of today. There is, for example, a lack of compact, robust and cost-effective read-out technology that combines high sensitivity with high dynamic range. Sensors that are good at detecting small amounts of analyte typically have poor dynamic range which is especially noticeable when the levels of analyte are large. A problem with AFM-based cantilever systems is that they are very large as they incorporate bulky free space optics requiring a sensor for each cantilever output. A problem with electrical cantilever systems is that they require extensive power on-chip electronics As is known in the art, an Atomic Force Microscope (AFM) consists of a cantilever with a pointed tip or probe at its end that is used to scan a sample surface. The cantilever is typically made of silicon or silicon nitride with a tip radius of curvature in the order of nanometers using micro-electromechanical fabrication techniques. When the tip is brought into proximity of the sample surface, forces between the tip and the sample lead to a deflection of the cantilever according to Hooke's law.

Interatomic forces between the probe tip and the sample surface cause the cantilever to deflect as the sample's surface topography (or other properties) change as the tip is scanned across the sample. A laser light reflected from the back of the cantilever measures the deflection of the cantilever. This information is fed back to a computer, which generates a map of topography and/or other properties of interest.

Various measurements can be made including measuring either the deflection of the cantilever (static mode) or a vibration frequency of the cantilever (dynamic mode). In some applications, the tip is coated with a thin film of ferromagnetic material that reacts to magnetic areas on the sample surface. Some applications include:

Measuring 3-dimensional topography of an integrated circuit device

Roughness measurements for chemical mechanical polishing

Analysis of microscopic phase distribution in polymers

Mechanical and physical property measurements for thin films

Imaging magnetic domains on digital storage media

Imaging of submicron phases in metals

Defect imaging in IC failure analysis

Microscopic imaging of fragile biological samples

Metrology for compact disk stampers

A problem with current AFMs is that the sensitivity is limited by shot noise in the optical detection system. Although Brownian motion of the cantilever is a contributor to the noise, in practice it is not a factor as the shot noise is substantially greater than the noise induced by Brownian motion. While noise induced by Brownian motion may be reduced by cooling the cantilever, this is not practical for current AFMs as it may interfere with the alignment of the optical system. A further problem is that, the process of measuring an entire surface of a sample is time consuming, as the probe tip must make many passes over the sample in order to build up an image.

Yet a further problem with current AFMs is that the probe often needs to be replaced, and each time the probe is replaced the optical detection system needs to be re-calibrated, which is a time consuming process.

There is therefore a need for an improved system and method of using cantilevers to perform sensitive measurements.

SUMMARY OF THE INVENTION

In one form, although not necessarily the only or the broadest form, the invention resides in an optical sensor including:

a MicroElectroMechanical Systems (MEMS) structure; and a grating coupled resonating structure positioned adjacent to the MEMS structure, the grating coupled resonating structure comprising an interrogating grating coupler configured to direct light towards the MEMS structure; wherein the interrogating grating coupler is two dimensional; and the interrogating grating coupler and the MEMS structure form an optical resonant cavity.

Preferably, the MEMS structure is a beam.

Preferably, the beam is a cantilever.

Preferably, the interrogating grating coupler includes a plurality of holes forming an array.

Preferably, the array is a regular shape. Preferably, the array forms a square. Preferably, the array forms a rectangle.

Preferably, the array is an irregular shape.

Preferably, the holes are etched in a Silicon on Insulator (SOI) layer.

Preferably, each hole is cylindrical in shape.

Preferably, the SOI layer is formed on a Buried Oxide (BOX) layer. Preferably, the BOX layer is formed on a substrate. In an alternate embodiment, the SOI layer is formed on the substrate.

Preferably, the grating coupled resonating structure includes an input grating coupler for inputting light into the optical sensor.

Preferably, the grating coupled resonating structure includes an output grating coupler for outputting light from the optical sensor.

Preferably, the input grating coupler is one dimensional. Preferably, the input grating coupler is two dimensional.

Preferably, the input grating coupler includes a plurality of holes forming an array.

Preferably, the output grating coupler is one dimensional. Preferably, the output grating coupler is two dimensional.

Preferably, the output grating coupler includes a plurality of holes forming an array.

Preferably, the cantilever includes an analyte selective coating.

In another broad form, the invention resides in a method of detecting a deflection of a MEMS structure, the method comprising the steps of:

inputting an optical signal into an interrogating grating coupler, the interrogating grating coupler being arranged to form a resonant cavity with the MEMS structure; and analyzing the optical signal output from the interrogating grating coupler to determine a deflection of the MEMS structure; wherein the interrogating grating coupler is two dimensional.

In another broad form, the invention resides in an apparatus for detecting a deflection of a beam, the apparatus comprising:

a beam having a first side and a second side; and a grating structure positioned adjacent the second side of the beam, the grating structure including an interrogating grating coupler configured to direct light towards the beam;

wherein the beam and the interrogating grating coupler form a resonant cavity, and light input to the resonant cavity is modulated according to the deflection of the beam.

In another broad form, the invention resides in a method for detecting a deflection of a beam, the method comprising the steps of:

inputting light into a resonant cavity formed between a beam and a grating structure of a sensor;

receiving light modulated by a deflection of the beam; and analysing the modulated light to determine the deflection of the beam.

Preferably, the beam is a cantilever.

In another embodiment, the invention resides in an apparatus for detecting a presence of one or more analytes in a sample, the apparatus comprising a first cantilever comprising an analyte selective coating that is selective to said one or more analytes, a first grating coupled resonating structure positioned adjacent to the cantilever and comprising a first interrogating grating coupler, wherein the first interrogating grating coupler and the cantilever form an optical resonant cavity.

Preferably, the cantilever is dynamic.

Alternatively, the cantilever is static.

Preferably, the apparatus further comprises a second grating coupled resonating structure wherein the second grating coupled resonating structure comprises a second interrogating grating coupler; and the second interrogating grating coupler and the cantilever form an optical resonant cavity.

Preferably, the second grating coupled resonating structure is positioned adjacent to the first grating coupled resonating structure on an axis substantially parallel to the cantilever.

Preferably, the apparatus further comprises a signal analyser for detection of the presence of one or more analytes in the sample.

Preferably, the signal analyser compares light modulated by the first grating coupled resonating structure and the cantilever with a plurality of predefined signals.

Preferably, the first grating coupled resonating structure provides an initial measurement, and the second grating coupled resonating structure provides a refinement of said initial measurement.

Preferably, the first grating coupled resonating structure and the second grating coupled resonating structure are used to determine a shape of the cantilever.

Optionally, the apparatus further comprises:
a second cantilever;
a second grating coupled resonating structure comprising a second interrogating grating coupler;
wherein the second interrogating grating coupler and the second cantilever form an optical resonant cavity.

Preferably, the first grating coupled resonating structure and the second grating coupled resonating structure are optically coupled in series.

Optionally, the first grating coupled resonating structure and the second grating coupled resonating structure are optically coupled in parallel.

In another form, the invention resides in a method of detecting the presence of one or more analytes in a sample. The method comprises the steps of applying the sample to a cantilever, wherein the cantilever comprises an analyte selective coating selective to the one or more analytes, passing an optical signal through a grating coupled resonating structure, wherein the grating coupled resonating structure is arranged to form a resonant cavity with the cantilever; and analyzing the optical signal.

Preferably, the cantilever is dynamic, and the step of analyzing the optical signal comprises determining the resonance frequency of the cantilever and comparing the resonance frequency to known resonant characteristics of the cantilever.

Alternatively, the cantilever is static, and the analysis step comprises determining a deflection of the cantilever.

Preferably, the cantilever is dynamic, and the step of analyzing the optical signal comprises determining the resonance frequency of the cantilever and comparing the resonance frequency to known resonant characteristics of the cantilever.

Preferably, the step of analyzing the optical signal comprises comparing the optical signal to a plurality of predefined signals.

Preferably, the method further comprises the steps of passing a second optical signal through a second grating coupled resonating structure, wherein the second grating coupled resonating structure is arranged to form a resonant cavity with the cantilever, and analyzing the second optical signal.

Preferably, the step of analysing the optical signal comprises estimating an initial cantilever deflection measurement, and the step of analyzing the second optical signal comprises refining the initial cantilever deflection measurement.

Preferably, the method further comprises the step of estimating a shape of said cantilever, wherein the step of analysing the optical signal comprises estimating a cantilever deflection measurement at a first position, and the step of analysing the second optical signal comprises estimating a cantilever deflection measurement at a second position.

In yet another form, the invention resides in a system for performing atomic force measurements including:
a sensor including:
a beam having a first side and a second side, the beam including a tip positioned on a surface of the first side for interacting with a sample; and
a grating structure positioned adjacent the second side of the beam, the grating structure including an interrogating grating coupler configured to direct light towards the beam;
a light source optically coupled to an input of the sensor for inputting light; and
an analyser coupled to an output of the sensor; wherein the beam and the interrogating grating coupler form a resonant cavity, a movement of the beam modulates the light source and the analyser determines a deflection of the beam according to the modulated light.

Preferably, the beam is a cantilever beam. Alternatively, the beam is fixed at opposite ends and includes a flexible portion between the ends. Preferably, the tip is positioned between the two ends of the beam.

Preferably, the modulated light is amplitude modulated. Alternatively or additionally, the modulated light is frequency modulated.

Preferably, the system includes a plurality of sensors.

Preferably, the system further includes a de-multiplexer wherein an input of the de-multiplexer is optically connected to the light source and each output of a plurality of outputs of the de-multiplexer is optically connected to a respective input of a grating structure of a respective sensor.

Preferably, the system further includes a multiplexer wherein each output of the plurality of grating structures of a respective sensor is optically connected to an input of the multiplexer, and the output of the multiplexer is connected to the analyse.

Preferably the de-multiplexer is a wavelength division de-multiplexer.

Preferably, light input into the multiplexer is separated into a plurality of discrete wavelengths and/or wavelength bands.

Preferably, each wavelength of the plurality of discrete wavelengths is modulated by a respective sensor.

In yet another form the invention resides in a method of performing atomic force measurements on a sample, the method including the steps of:
inputting light into a resonant cavity formed between a beam and a grating structure of a sensor;
receiving at an analyser light modulated by a movement of the beam; and
analysing the modulated light to determine a characteristic of the sample.

Preferably, the characteristic is a topography of the sample.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which:

FIG. 16 shows a sectional view through section A-A of FIG. 15, according to an embodiment of the present invention;

FIG. 17 shows a sectional view through section B-B of FIG. 15 according to an embodiment of the present invention; and FIG. 18 shows a side sectional view of another embodiment of a two dimensional interrogating grating coupler, according to an embodiment of the present invention.

DETAILED DESCRIPTION

Figure 1:
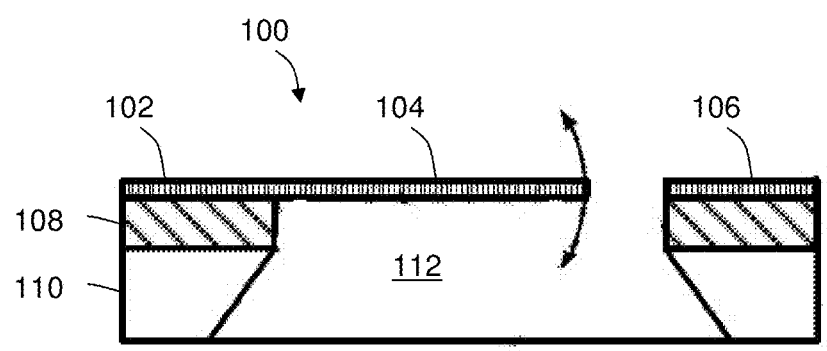
FIG. 1 shows a side sectional view of an optical microcantilever waveguide, according to the prior art.

While the present invention is open to various modifications and alternative constructions, the example embodiments shown in the drawings will be described herein in detail. It is to be understood, however, there is no intention to limit the invention to the particular example forms disclosed. On the contrary, it is intended that the invention cover all modifications, equivalences and alternative constructions falling within the spirit and scope of the invention as expressed in the appended claims.

FIG. 1 shows a side sectional view of an optical microcantilever waveguide 100, according to the prior art. The optical microcantilever waveguide 100 comprises a fixed component 102 and a dynamic component 104. The fixed component 102 is attached to an insulator 108 such as for example $SiO_2$ or $Si_3N_4$. The insulator 108 is attached to a substrate 110 such as for example a Si substrate. This layered structure allows for the simple construction of the optical microcantilever waveguide 100 through layering of the substrate 110, the insulator 108 and the fixed component 102 and the dynamic component 104 of the optical cantilever waveguide 100, and by then etching away an area of the insulator 108 (and possibly also an area of the substrate 110) forming a void 112 under the dynamic component 104 of the optical microcantilever waveguide 100. The dynamic component 104 of the microcantilever waveguide 100 is optically coupled to a fixed waveguide 106.

The dynamic component 104 is free to move above the void 112 in the insulator 108. Upon adsorbtion of an analyte, the mass of the dynamic component 104 of the optical microcantilever waveguide 100 changes. This change in mass results in a change of a resonance frequency of the optical microcantilever waveguide 100.

Light enters at an end of the fixed component 102 of the optical microcantilever waveguide 100 and propagates along the waveguide 100 to the dynamic component 104. Light exits the dynamic component 104 in a direction towards the fixed waveguide 106.

In a dynamic mode, the light entering the fixed waveguide 106 is amplitude modulated as a result of a coupling loss between the dynamic component 104 and the fixed waveguide 106 that is in close proximity to the dynamic component 104, which loss occurs as the dynamic component 104 vibrates. The light entering the fixed waveguide 106 is nominally modulated at twice the vibration frequency of the dynamic component 104 for symmetric vibration. Alternatively, in a static mode, the dynamic component 104 of the optical microcantilever waveguide 100 may change shape upon adsorbtion of an analyte. In this case the light entering the fixed waveguide 106 has an amplitude based upon the shape of the dynamic component 104 of the optical microcantilever waveguide 100.

The light entering the fixed waveguide 106 is analysed to detect the presence of an analyte on the optical microcantilever waveguide 100. The light may be compared to light with known characteristics, such as for example light modulated due to the presence of an analyte. Alternatively, the resonance frequency or shape of the optical microcantilever waveguide 100 may be estimated and compared to predetermined characteristics.

According to some embodiments, the present invention resides in an apparatus for detecting a presence of one or more analytes in a sample. The apparatus comprises a cantilever and a grating coupled resonating structure positioned adjacent to the cantilever. The cantilever comprises an analyte selective coating that is selective to the one or more analytes. The grating coupled resonating structure comprises an interrogating grating coupler which forms an optical resonant cavity with the cantilever.

An advantage of the present invention is the ability to economically have a very large number of sensors on a small surface, enabling efficient detection on multiple analytes. Furthermore it does not require bulky free space optics or extensive power on-chip electronics.

Figure 2:
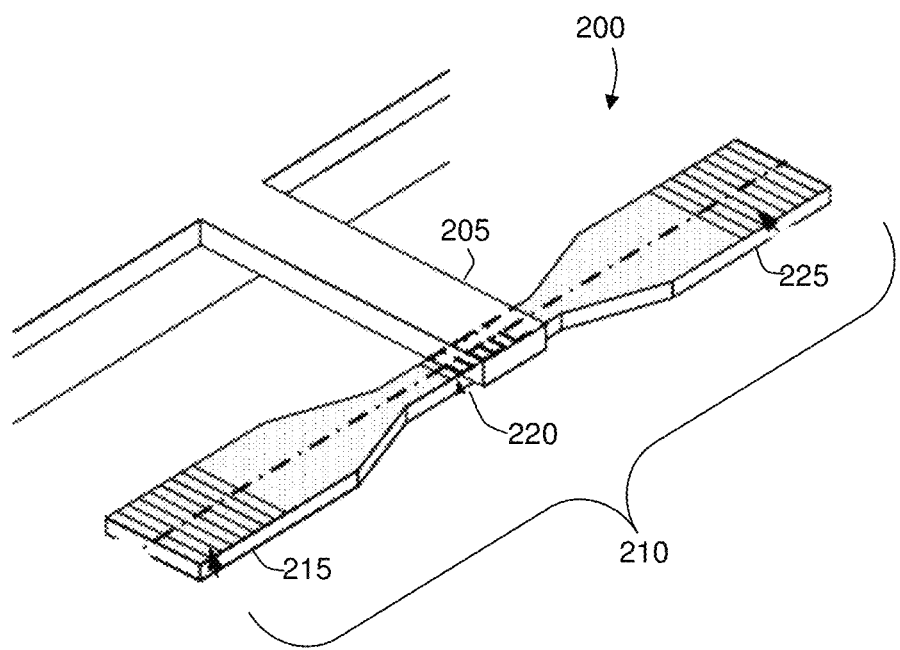
FIG. 2 shows a top perspective view of an optical microcantilever sensor according to an embodiment of the invention.
Figure 3:
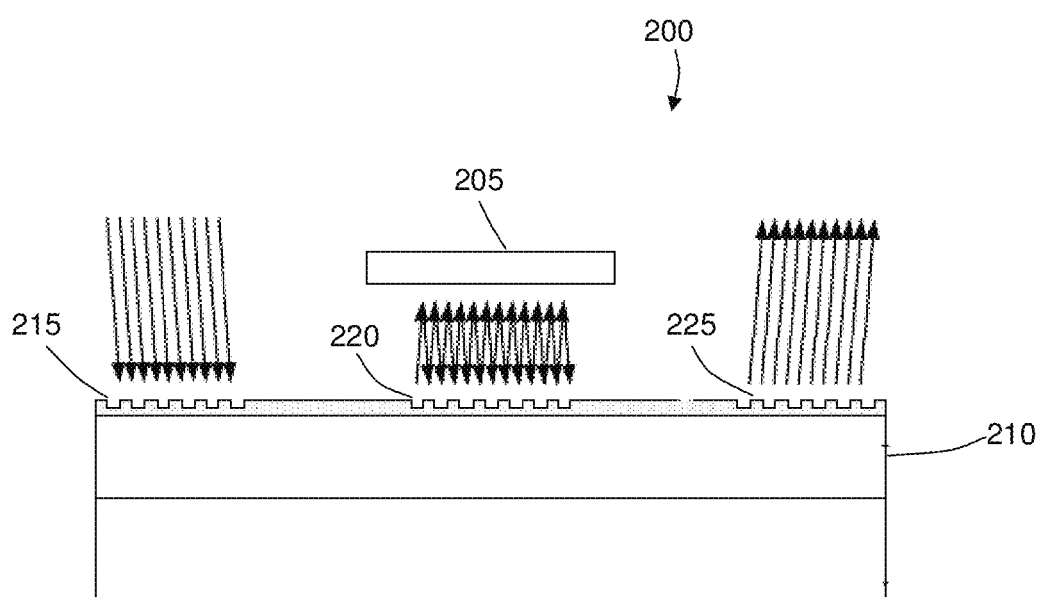
FIG. 3 shows a front sectional view of the optical microcantilever sensor according to an embodiment of the invention.

FIG. 2 shows a top perspective view and FIG. 3 shows a front sectional view of an optical microcantilever sensor 200 according to an embodiment of the invention. As shown in FIG. 2 and FIG. 3, the optical microcantilever sensor 200 comprises a cantilever 205 and a grating coupled resonating structure 210. The grating coupled resonating structure 210 comprises an input grating coupler 215, an interrogating grating coupler 220 and an output grating coupler 225. The interrogating grating coupler 220 is placed directly under and adjacent to the cantilever 205. The cantilever 205 comprises an analyte selective coating on a surface of the cantilever 205 and a reflective surface 207, where the reflective surface 207 is opposite the interrogating grating coupler 220. However it should be appreciated that the cantilever 205 may be a beam, or a cantilever without an analyte selective coating. Thus the present invention may be used to detect a movement of any type of beam or cantilever.

The input grating coupler 215 is optically connected to the interrogating grating coupler 220 and the interrogating grating coupler 220 is optically connected to the output grating coupler 225. The output grating coupler 225 is optically connected to a signal analyser (not shown), for example through an optical fibre.

Referring to FIG. 3, arrows illustrate the path of light through the optical microcantilever sensor 200.

Light is coupled to the input grating coupler 215 from a light source, via an optical waveguide or an optical fibre, for example. The light propagates along the grating coupled resonating structure 210 to the interrogating grating coupler 220 and out of the interrogating grating coupler 220 in a near perpendicular direction towards the cantilever 205 and is then reflected back to the grating coupler 220. The light then propagates along the grating coupled resonating structure 210 to the output grating coupler 225.

The cantilever 205 and interrogating grating coupler 220 form a resonant cavity such that the amount and/or frequency of light coupled to the output grating coupler 225 is a function of the separation of the interrogating grating coupler 220 and the cantilever 205.

The light is output from the grating coupled resonating structure 210 via the output grating coupler 225 so that it may be analysed in real time or recorded in the analyser or on a computer, for example, for analysis at a later time.

When a sample is applied to the cantilever 205, adsorbtion of an analyte may occur depending on the analyte selective coating and a composition of the sample.

A pattern or shape of the interrogating grating coupler 220, for example dimensions of grooves of the interrogating grating coupler 220, determines a modulation of light resonating between the interrogating grating coupler 220 and the cantilever 205. Additionally, a change in distance between the cantilever 205 and the interrogating grating coupler 220 causes a change in the modulation of the light output from the output grating coupler 225 due to constructive or destructive interference with the light in the grating coupled resonating structure 210.

A change in mass of the cantilever 205 occurs upon adsorbtion of the analyte. In a dynamic mode of operation, the change in mass results in a change in resonance frequency of the cantilever 205 which may be compared to when the analyte is not present. The resonance frequency of the cantilever can be determined at the output grating coupler 225 through resonant excitation of the cantilever 205.

Alternatively, in a static mode of operation, the presence of an analyte causes a change in shape of the cantilever 205. The change in shape of the cantilever 205 causes a change in the distance between the cantilever 205 and the interrogating grating coupler 220 and hence change in the light at the output grating coupler 225.

The signal analyser, which indicates the presence and concentration of the analyte in the sample, uses analysis of the light to estimate the resonance frequency of the cantilever 205, or in the case of a static cantilever the shape of the cantilever 205.

The resonance frequency of the cantilever 205 in dynamic mode operation, or the shape of the cantilever 205 in static mode, may be compared to known characteristics of the cantilever 205 to determine whether an analyte is present or not. Known characteristics of the cantilever 205 include resonance frequency without the presence of an analyte, resonance frequencies with the presence of a particular amount of analyte or concentration, shape without the presence of an analyte, and shapes with the presence of a particular amount of analyte or concentration.

In an embodiment of the invention, the resonance frequency, height or position need not be calculated or estimated explicitly for each cantilever and measurement. Predefined signals of the cantilever at, for example, different resonance frequencies, heights or positions may be compared directly to the signal in the analysis step.

Figure 4:
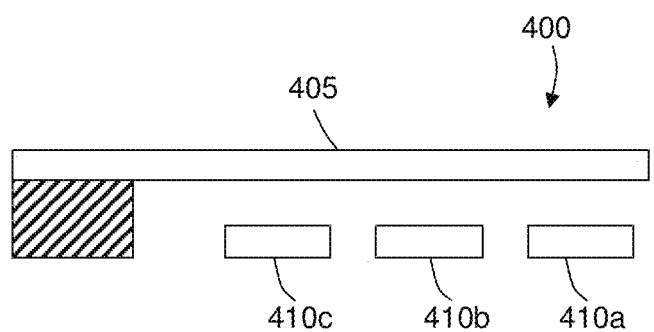
FIG. 4 shows a side sectional view of an optical microcantilever sensor according to a second embodiment of the invention.

FIG. 4 shows a side sectional view of an optical microcantilever sensor 400 according to a second embodiment of the invention. The optical microcantilever sensor 400 comprises a cantilever 405 and a first, second and third grating coupled resonating structure 410a, 410b and 410c, respectively, which are each specific examples of the grating coupled resonating structure 210 of FIG. 2. Similarly, the cantilever 405 is a specific example of the cantilever 205 of FIG. 2.

The first grating coupled resonating structure 410a, placed under a distal end of the cantilever 405, can be used to measure fine changes in shape or fine movements in the cantilever 405.

The second grating coupled resonating structure 410b is positioned adjacent to the first grating coupled resonating structure 410a on an axis substantially parallel to the cantilever 405. The second grating coupled resonating structure 410b, placed under a central part of the cantilever 405, can be used when larger changes in shape or large movements are to be measured, possibly in combination with the first grating coupled resonating structure 410a. In this case the second grating coupled resonating structure 410b provides a refinement of an initial measurement of the first grating coupled resonating structure 410a.

The third grating coupled resonating structure 410c is positioned adjacent to the second grating coupled resonating structure 410b on an axis substantially parallel to the cantilever 405. The third grating coupled resonating structure 410c is placed under a proximal end of the cantilever 405 and can be used when larger changes in shape or larger movements are to be measured, possibly in combination with the first and second grating coupled resonating structures 410a and 410b. In this case the third grating coupled resonating structure 410c provides a further refinement of the initial measurement of the first grating coupled resonating structure 410a and the refinement provided by the second grating coupled resonating structure 410b.

As would be readily understood by those skilled in the art, any number of grating coupled resonating structures 410 may be placed under a single cantilever, and at any position, without deviating from the present invention.

The exemplary embodiments illustrated in FIG. 2, FIG. 3 and FIG. 4 are applicable to both static and dynamic cantilevers 205, 405, and in both gaseous and aqueous environments. Furthermore, the grating coupled resonating structure 210, 410a, 410b, 410c can be oriented arbitrarily with respect to the cantilever 205, 405, and the design of the cantilever 205, 405 can be decoupled from the design of the grating coupled resonating structure 210, 410a, 410b, 410c. A further valuable capability of this approach is that the multiple grating coupled resonating structures 210, 410a, 410b, 410c under the single cantilever 205, 405, as described in FIG. 4, allows for the shape of the cantilever 205, 405 to be measured with greater precision.

Since an analyte can initially be adsorbed anywhere along the analyte selective coating of the cantilever 205, 405, a change in shape of the cantilever 205, 405 can be used as an early indication of the presence of the analyte. Further, as is discussed further in FIG. 5, it may be advantageous to have multiple grating coupled resonating structures to enhance a dynamic range of the optical microcantilever sensor 200, 400.

Figure 5:
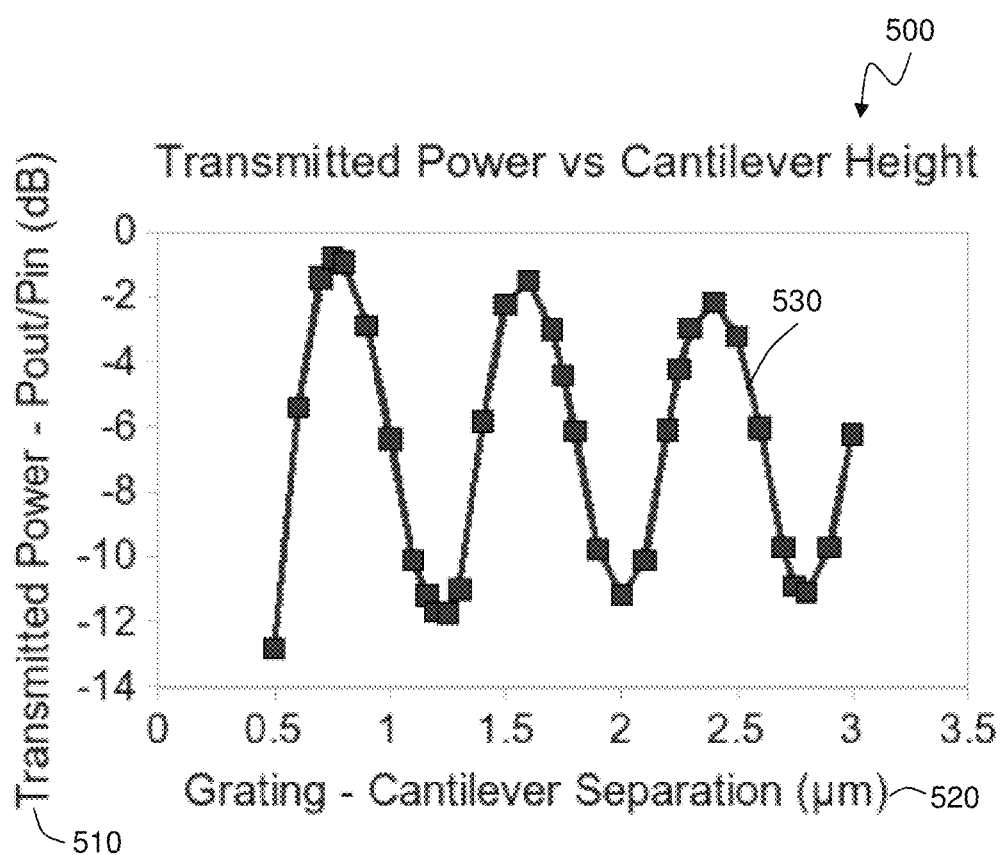
FIG. 5 is a graph showing the periodic nature of transmission power of a signal according to an embodiment of the invention.

FIG. 5 is a graph 500 showing the periodic nature of transmission power 510 of a signal 530 according to an embodiment of the invention, with respect to a separation 520 between the cantilever 205, 405 and the grating coupled resonating structure 210, 410a, 410b, 410c. As can be seen in the figure, separations of 0.5, 1.25, 2 and 2.75 micrometers, for example, have similar transmission powers 510. This ambiguity can however be removed, while still maintaining high sensitivity, by measuring the displacement of the cantilever 205, 405 at multiple positions. FIG. 4 illustrates an example where multiple grating coupled resonating structures 210, 410a, 410b, 410c are placed under a single cantilever. Such configurations allow for Vernier-like calculations to be made.

Figure 6:
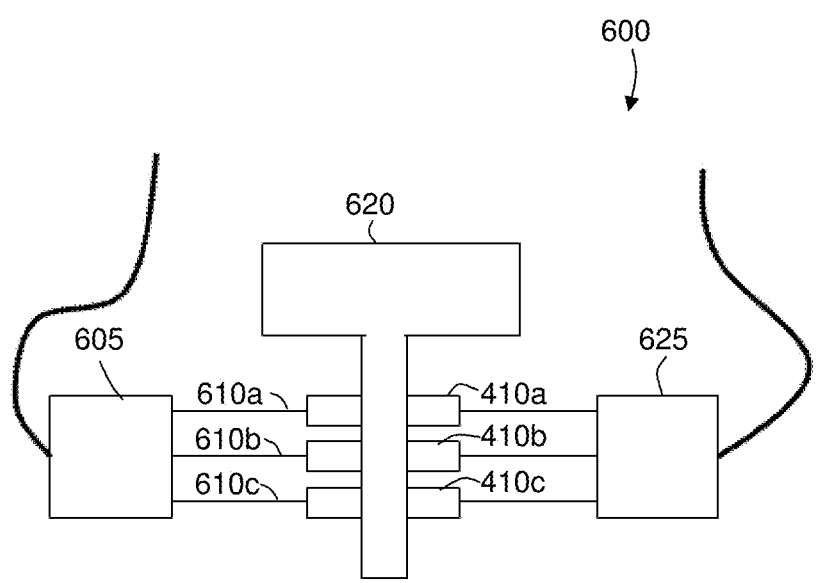
FIG. 6 shows a schematic diagram of a top view of the embodiments of FIG. 4.

FIG. 6 shows a schematic diagram of a top view of the embodiments of FIG. 4. The optical microcantilever sensor 600 comprises a wavelength division de-multiplexer 605, the wavelength division de-multiplexer 605 comprising three optical outputs 610a, 610b, 610c, the three grating coupled resonating structures 410a, 410b, 410c, a cantilever 405 and a wavelength division multiplexer 625.

An optical input is optically coupled to the wavelength division de-multiplexer 605. The wavelength division de-multiplexer 605 processes light from the optical input and splits the light into a plurality of subsignals, each subsignal having a particular wavelength or plurality of wavelengths. In this example, the wavelength division de-multiplexer 605 has the three optical outputs 610a, 610b, 610c, each carrying light corresponding to a different wavelength or wavelength band.

The optical outputs 610a, 610b, 610c are optically coupled to the grating coupled resonating structures 410a, 410b, 410c. Each grating coupled resonating structure 410a, 410b, 410c is connected in parallel and forms an optical resonance cavity with the cantilever 405. The wavelength division multiplexer 625 additively combines the light output from grating coupled resonating structures 410a, 410b, 410c such that an output signal of the wavelength division multiplexer 625 comprises a single light signal comprising multiple wavelengths. By using different wavelengths changes a position of the peaks and nulls in FIG. 5 due to the constructive and destructive interference being dependent on the wavelength of operation.

Analysis of an individual grating coupled resonating structure 410a, 410b, 410c, may be performed by using pre-known characteristics of the grating coupled resonating structure 410a, 410b, 410c. These characteristics include, for example, a wavelength throughput of the grating coupled resonating structure 410a, 410b, 410c.

Figure 7:
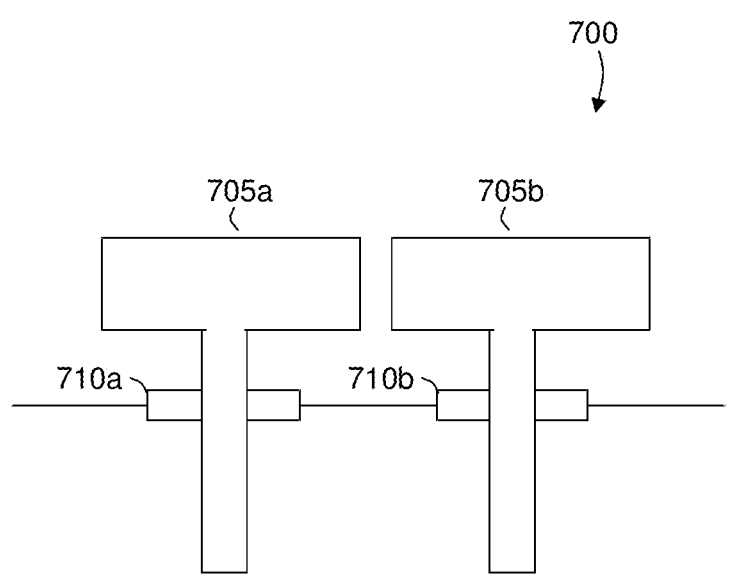
FIG. 7 shows a schematic diagram of an optical microcantilever sensor according to a third embodiment of the invention.

FIG. 7 shows a schematic diagram of an optical microcantilever sensor 700 according to a third embodiment of the invention. The optical microcantilever sensor 700 comprises two cantilevers 705a, 705b and two grating coupled resonating structures 710a, 710b.

The grating coupled resonating structures 710a, 710b form resonant cavities with the cantilevers 705a, 705b. The grating coupled resonating structure 710a is optically coupled to the grating coupled resonating structure 710b in series, i.e. an output of the first grating coupled resonating structures 710a is connected in an input of the second grating coupled resonating structures 710b.

Cantilever and grating coupled resonating structure pairs, for example 705a and 710a, or 705b and 710b, may be analysed individually. This is advantageous as each pair may be sensitive to a different analyte. The analysis may be performed by using pre-known characteristics of the grating coupled resonating structure 710a, 710b or the cantilever 705a, 705b. These characteristics include, for example, a resonance frequency of the cantilever 705a, 705b and a wavelength throughput of the grating coupled resonating structure 710a, 710b given a separation to the cantilever 705a, 705b. In addition each cantilever 705a, 705b can have different dimensions to shift a natural resonant frequency of each cantilever 705a, 705b.

Figure 8:
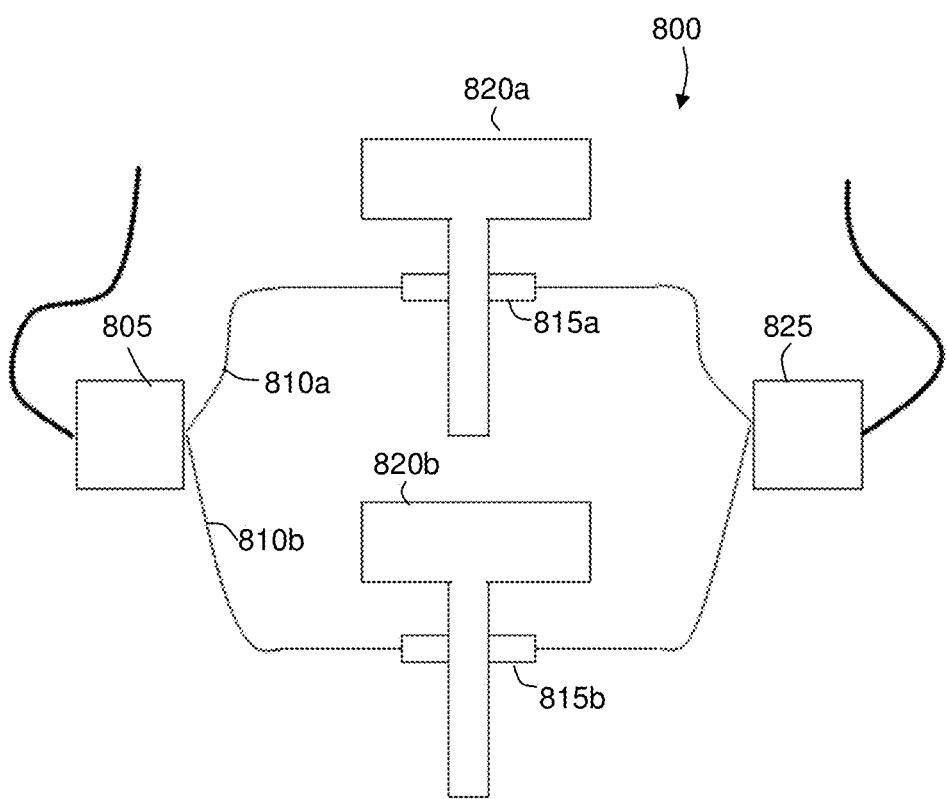
FIG. 8 shows a schematic diagram of an optical microcantilever sensor according to a fourth embodiment of the invention.

FIG. 8 shows a schematic diagram of an optical microcantilever sensor 800 according to a fourth embodiment of the invention.

The optical microcantilever sensor 800 comprises a wavelength division de-multiplexer 805, the wavelength division de-multiplexer 805 comprising two optical outputs 810a, 810b, two grating coupled resonating structures 815a, 815b, two cantilevers 820a, 820b and a wavelength division multiplexer 825.

An optical input is optically coupled to the wavelength division de-multiplexer 805. The wavelength division de-multiplexer 805 processes light from the optical input and splits the light into a plurality of subsignals, each subsignal having a particular wavelength or plurality of wavelengths. In this example, the wavelength division de-multiplexer 805 has the two optical outputs 810a, 810b, each carrying light corresponding to a different wavelength or wavelength band.

The optical outputs 810a, 810b are optically coupled to the grating coupled resonating structures 815a, 815b respectively. The grating coupled resonating structures 815a, 815b are similar to the grating coupled resonating structures 210, 410a, 410b, 410c. Each grating coupled resonating structure 815a, 815b forms an optical resonance cavity with the cantilevers 820a, 820b, respectively. The wavelength division multiplexer 825 additively combines the light output from grating coupled resonating structures 815a, 815b such that an output signal of the wavelength division multiplexer 825 comprises a single light signal comprising multiple wavelengths.

Analysis of an individual cantilever grating coupled resonating structure combination, for example 815a/820a or 815b/820b, which are connected in parallel, may be performed by using pre-known characteristics of the grating coupled resonating structure 815a, 815b or the cantilever 820a, 820b. These characteristics include, for example, a resonance frequency of the cantilever 820a, 820b and a wavelength throughput of the grating coupled resonating structure 815a, 815b.

Figure 9:
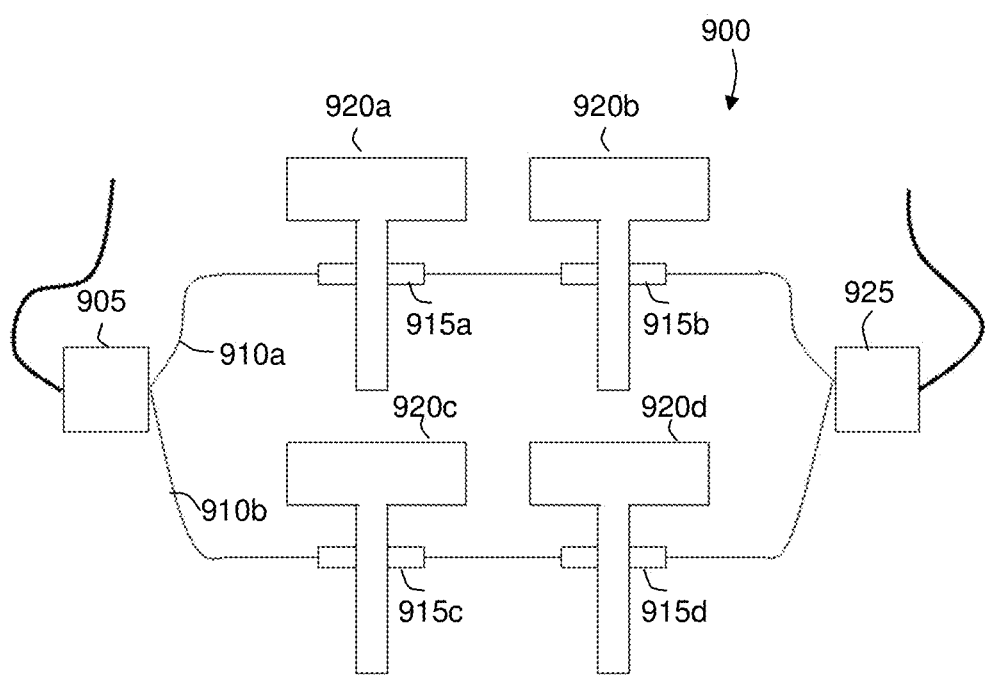
FIG. 9 shows a schematic diagram of an optical microcantilever sensor 900 according to a fifth embodiment of the invention.

FIG. 9 shows a schematic diagram of an optical microcantilever sensor 900 according to a fifth embodiment of the invention.

The optical microcantilever sensor 900 comprises a wavelength division de-multiplexer 905, the wavelength division de-multiplexer 905 comprising two optical outputs 910a, 910b, four grating coupled resonating structures 915a, 915b, 915c, 915d, four cantilevers 920a, 920b, 920c, 920d and a wavelength division multiplexer 925. The optical microcantilever sensor 900 is similar to the embodiments described in FIG. 7 and FIG. 8, except for that the cantilevers 920a, 920b, 920c, 920d and grating coupled resonating structures 915a, 915b, 915c, 915d are coupled in a series and parallel configuration.

The terms 'series' and 'parallel' are used in this specification. Series refers to the case where an output of a first grating coupled resonating structure is optically connected to an input of a second grating coupled resonating structure. Parallel refers to the case where an input is shared between a first and second grating coupled resonating structure. Parallel connections include the case where the first grating coupled resonating structure uses or modifies a first part of the input, and the second grating coupled resonating structure uses or modifies a second part of the input, even where a series physical connection exists.

Additionally, as is understood by a person skilled in the art, any number of parallel and series connections may exist on a single sensor.

As will be understood by those having ordinary skill in the art, in light of the present description, advantages of the present invention include the ability to economically have a very large amount of sensors on a small surface, enabling efficient detection on multiple analytes. Furthermore, the detection of analytes with high precision and fidelity is possible. These efficient sensors may be used for the efficient and economical detection of pesticides or other chemicals in food, for efficient detection of explosives, narcotics or other elicit substances just to name a few examples.

Figure 10:
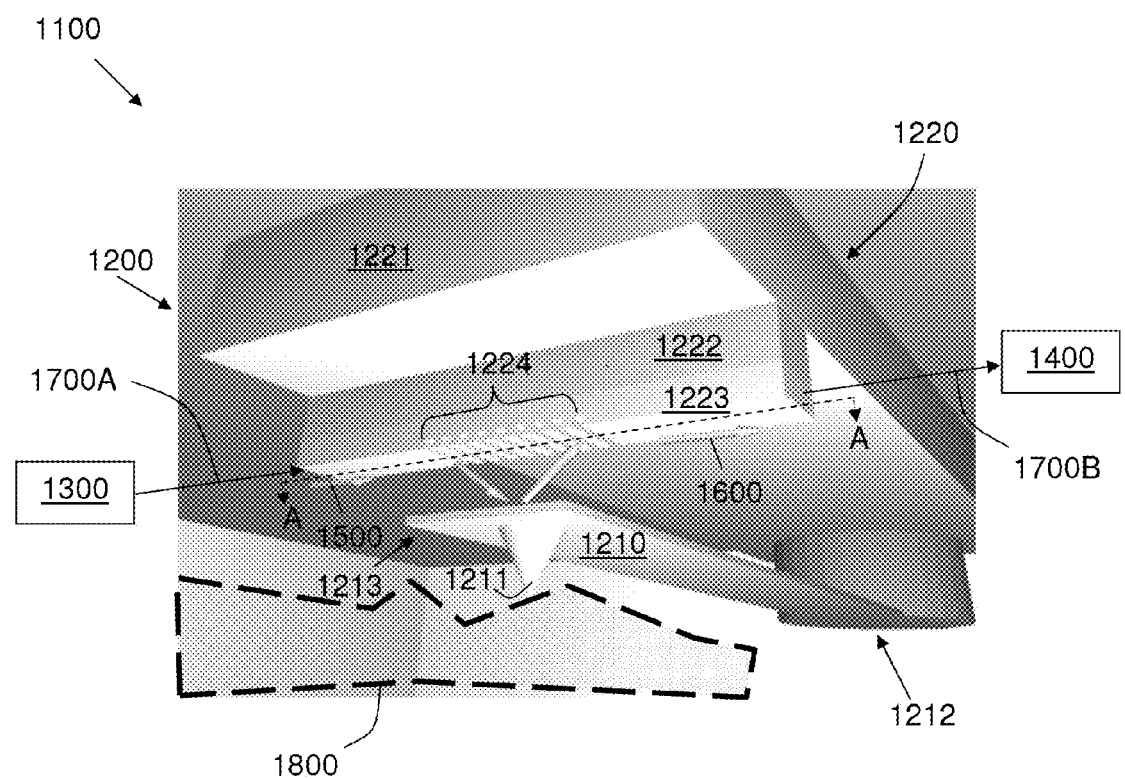
FIG. 10 is a bottom perspective view of a system for performing atomic force measurements.

FIG. 10 is a bottom perspective view of a system 100 for measuring Atomic Force according to a further embodiment of the present invention.

Figure 11:
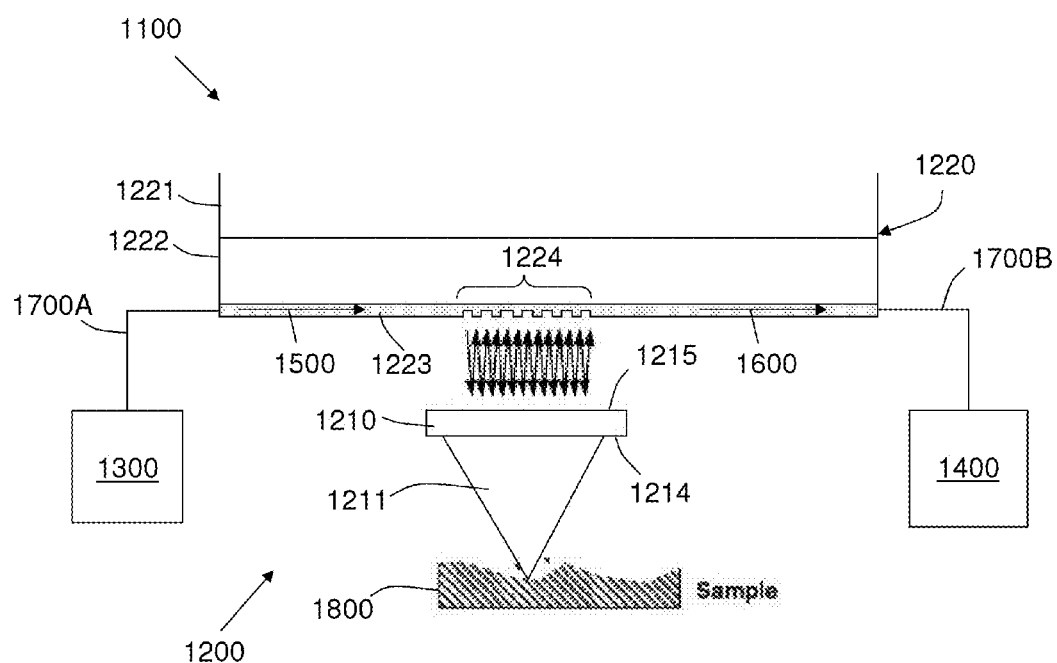
FIG. 11 is a cross-sectional end view of a sensor of FIG. 10.

FIG. 11 is a cross-sectional end view through section A-A of FIG. 10. Referring to FIGS. 10 and 11, the system 1100 includes a sensor 1200, a light source 1300 and an analyser 1400. The light source 1300 is connected to an input of the sensor 1200 by an optical waveguide 1700A such as an optical fibre. An output of the sensor 1200 is connected to the analyser 1400 by an optical waveguide 1700B such as an optical fibre.

In one embodiment, the sensor 1200 is made using micro-electro-mechanical systems (MEMS) technology and includes a beam in the form of a cantilever beam 1210 and a grating structure 1220 positioned adjacent the cantilever beam 1210. The cantilever beam 1210 is planar and includes a tip 1211 which is pointed. The cantilever beam 1210 includes a first side 1214 and a second side 1215. The tip 1211 is positioned on the first side 1214 of the cantilever beam 1210 and towards a distal end 1213 of the cantilever beam 1210. The tip 1211 extends away from the cantilever beam 1210 towards a sample 1800 to be measured. A proximal end 1212 of the cantilever beam 1210 is fixed allowing the distal end 1213 to flex as the tip 1211 is moved over the sample 1800.

In another embodiment (not shown), the beam is fixed at both the distal end and the proximal end but allowing the beam to flex. A tip is positioned in between the distal end and the proximal end. Preferably the tip is positioned mid-way between the distal end and the proximal end. However it should be appreciated that the tip may be positioned anywhere between the distal end and the proximal end. By fixing the beam at both ends, Brownian motion is reduced, and sensitivity of a measurement is increased.

In one embodiment, the grating structure 1220 uses Silicon on Insulator (SOI) technology and includes a substrate 1221, a buried oxide layer 1222 and a waveguide layer 1223. Furthermore, the substrate 1221 and the waveguide layer 1223 are made from silicon. The buried oxide layer 1222 is formed on the substrate 1221 and the waveguide layer 1223 is formed on the buried oxide layer 1222. The waveguide layer 1223 includes grooves to form an interrogating grating coupler 1224 and the interrogating grating coupler 1224 is positioned adjacent the second side 1215 of the cantilever beam 1210. The interrogating grating coupler 1224 is similar to the interrogating grating coupler 220 shown in FIGS. 2 and 3. In one embodiment, the waveguide layer 1223 is 220 nm thick fabricated over a 2000 nm buried oxide layer 1222 using an infra-red light source 1300. However it should be appreciated that other thicknesses may be used, for example between 100 nm and 2000 nm.

Although the grating structure 1220 has been described in relation to SOI technology, a person skilled in the art will appreciate that the grating structure 1220, including the waveguide layer 1223 and the buried oxide layer 222, may be made from many other materials. The main requirement is that the waveguide layer 1223 has a higher refractive index than the buried oxide layer 1222 so as to get the total internal reflections in the waveguide. For example, the waveguide layer 1223 may also be made from, but is not limited to, Germanium (Ge) and Silicon Oxy Nitride and the buried oxide layer 222 may be made from SU-8, Silicon dioxide (SiO2) or Magnesium Oxide (MgO). In addition, the thicknesses used to fabricate the waveguide layer 1223 and the buried oxide layer 1222 depend on the materials used and the wavelength of the light source 1300.

Typically a gap between the interrogating grating coupler 1224 and the cantilever beam 1210 is between 0.05 and 10 μm. However it should be appreciated that other distances may be used depending on the wavelength of the light source 1300 and the types of materials used for the grating structure 1220.

Although in the example above the sensor 1200 has been designed using a light source 1300 in the infra-red band (with a wavelength of between 390 nm to 700 nm), it should be appreciated that the light source 1300 may produce light in the visible band (with a wavelength between 390 nm to 750 nm) or the ultra-violet band (with a wavelength between 100 nm to 400 nm).

A pattern or shape of the interrogating grating coupler 1224, for example dimensions of grooves of the interrogating grating coupler 1224, determines a resonance of light resonating between the interrogating grating coupler 1224 and the cantilever beam 1210.

In use, the unmodulated light 1500 is input to the sensor 1200. The unmodulated light 1500 propagates along the silicon waveguide layer 1223 until the unmodulated light 1500 exits the waveguide layer 1223 towards the cantilever beam 1210 at the interrogating grating coupler 1224. The interrogating grating coupler 1224 couples and directs light out of the waveguide 1223 towards the cantilever beam 1210 and couples light reflected from the second side 1215 of the cantilever beam 1210 back into the waveguide thereby forming a resonant cavity with the cantilever beam 1210. As the cantilever beam 1210 moves towards and away from the interrogating grating coupler 1224, an intensity and/or frequency of light output to the analyser 1400 is modulated as a function of the separation between the interrogating grating coupler 1224 and the cantilever beam 1210. From the modulation, the analyser 1400 may determine a displacement of the cantilever beam 1210 in order, for example, to determine a topography. In some embodiments the second side 1215 of the cantilever beam 1210, is coated with a reflective material such as gold in order to increase the reflectivity.

Although referred to as unmodulated light, it should be appreciated that the light input to the sensor 1200 may be modulated with a first modulation. As the first modulated light passes through the sensor 1200 it is modulated by a second modulation. The second modulation may then be analysed by the analyser 1400 in order to determine a displacement of the cantilever beam 1210

It should be appreciated that in order to perform a scan, the sample 1800 may be fixed and the sensor 1200 moved across the sample 1300 under the control of the analyser 1400. Alternatively, the sample 1800 may be moved under the control of the analyser 1400 and the sensor 1200 may be stationary.

An electrostatic element may be used to control an initial position of the beam, (or an initial optical resonant cavity length) so as to tune the resonance of the optical cavity to its most sensitive position. An electrode is placed underneath the beam or cantilever beam 1210, but not over the grating structure 1220. The voltage between the electrode and the metal on the underside of the beam is then controlled to attract or repel the beam as necessary.

Figure 12:
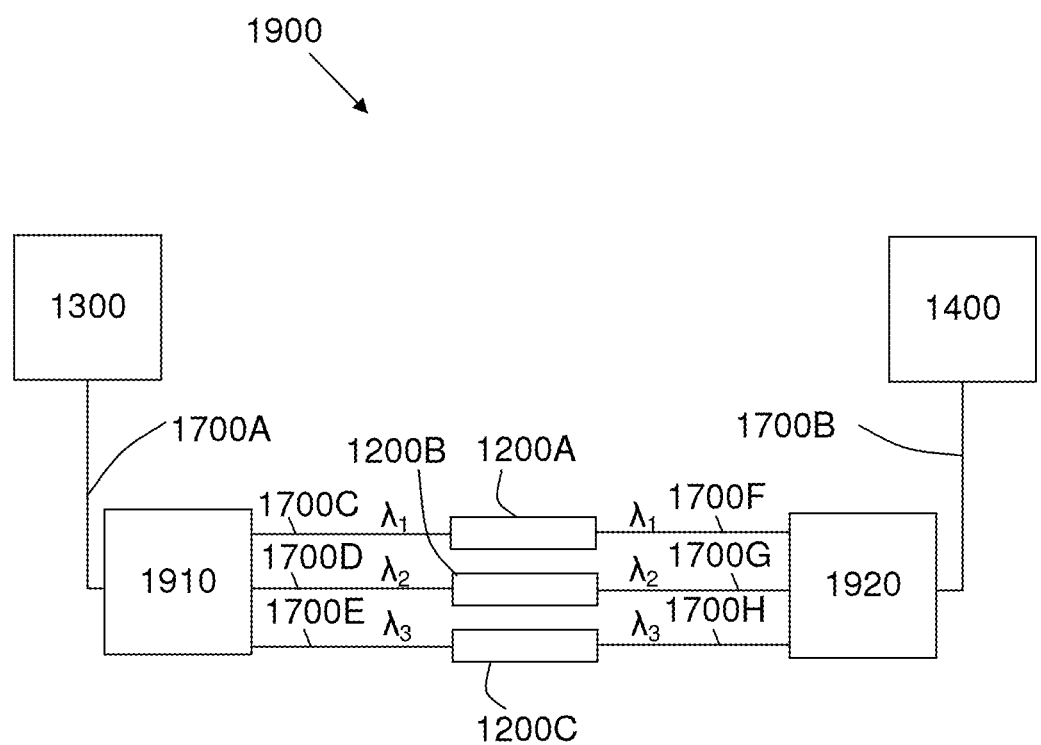
FIG. 12 is a block diagram illustrating a system of an array of the sensors shown in FIGS. 10 and 11 for performing atomic force measurements.

The sensor 1200 of the present invention may be used in an array in order to measure larger sections of the sample 1800. FIG. 12 is a block diagram illustrating a system of an array of sensors 2100 shown in FIGS. 10 and 11 for performing atomic force measurements according to an embodiment of the present invention. The system 1900 includes a plurality of sensors 1200A, 1200B, 1200C formed in a row. However it should be appreciated that the sensors 1200A, 1200B, 1200C may be positioned in any suitable arrangement.

In this embodiment, the light source 1300 is connected to a wavelength division de-multiplexer 1910 via a single optical waveguide 1700A. The wavelength division de-multiplexer 1910 separates the light source 1300 into a plurality of discrete wavelengths or wavelength bands $\lambda_1$, $\lambda_2$ and $\lambda_3$. Each output of the wavelength division de-multiplexer 1910 is connected to a respective sensor 1200A, 1200B, 1200C by a respective optical waveguide 1700C, 1700D, 1700E in order to couple the light at each wavelength $\lambda_1$, $\lambda_2$, $\lambda_3$ to a respective grating structure 1220 of a respective cantilever sensor 1200A, 1200B, 1200C. As each cantilever beam 1210 of a respective sensor 1200A, 1200B, 1200C moves it modulates the light at the respective wavelength or wavelength band $\lambda_1$, $\lambda_2$, $\lambda_3$.

The modulated light 1600 at each wavelength $\lambda_1$, $\lambda_2$, $\lambda_3$ is then multiplexed by a multiplexer 1920. Each sensor 1200A, 1200B, 1200C is connected to the multiplexer 1920 by a respective optical waveguide 1700F, 1700G, 1700H such as a waveguide or an optical fibre. An output of the multiplexer 1920 is connected to the analyser 1400 by optical waveguide 1700B and the modulated light at each wavelength $\lambda_1$, $\lambda_2$, $\lambda_3$ is passed to the analyser 1400. The analyser 1400 analyses the modulated light 1600 at each discrete wavelength or wavelength band $\lambda_1$, $\lambda_2$, $\lambda_3$ to determine a movement of each sensor 1200A, 1200B, 1200C and accordingly determine a characteristic of the sample 1800.

In another embodiment, the light from the light source 1300 may not be de-multiplexed into separate wavelengths; rather each sensor 1200 in the array may be supplied from its own light source 1300 or with a same wavelength of light from a same light source 1300. Furthermore, an output from each sensor 1200 may connect to a separate analyser 400, and each output analysed using a computer for example.

According to certain embodiments, the system 1100 includes a movement sensor (not shown), to determine the relative motion between the sensor 1200 and the sample 1800. This enables the determination of a contour of a sample irrespective of the rate of movement of the sample.

Figure 13:
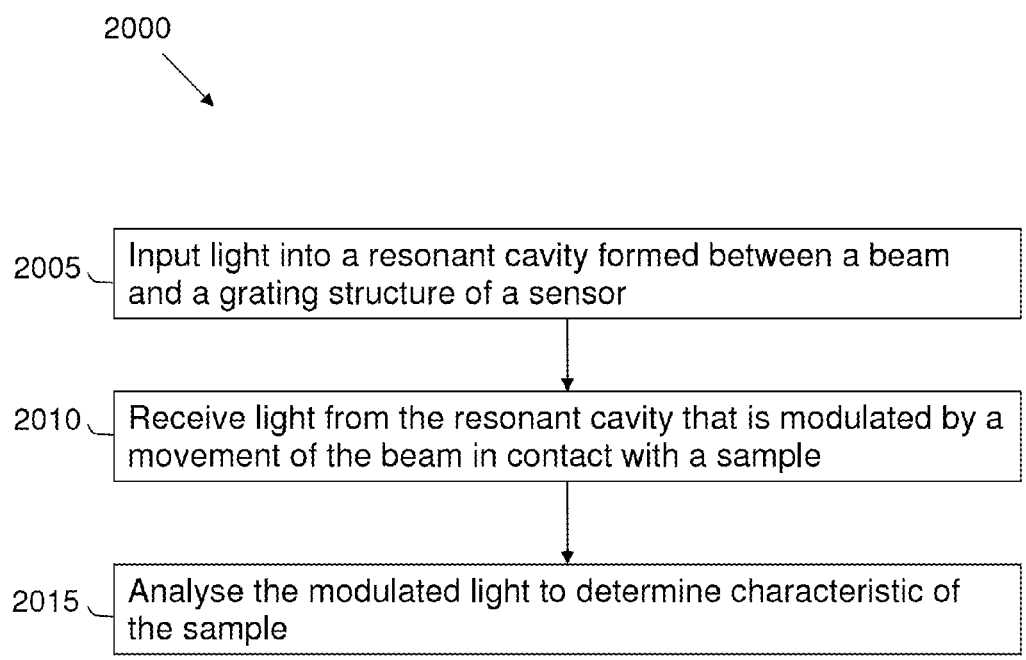
FIG. 13 illustrates a method of performing atomic force measurements on an object, according to an embodiment of the present invention.

FIG. 13 illustrates a method 2000 of performing atomic force measurements on an object, according to an embodiment of the present invention.

At step 2005, light is input into a resonant cavity formed between a beam and a grating structure of the sensor. A tip of the beam is positioned adjacent to and in contact with the object, such that the beam moves according to a contour of the sample.

At step 2010, the light from the resonant cavity is received at an analyser, the light modulated according to a position of the beam.

At step 2015, the modulated light is analysed to determine a contour of the sample.

Steps 2005-2015 are advantageously performed on multiple points of the object, either sequentially, for example through movement of the beam across the object, in parallel, for example through the use of several beams and resonance cavities, or through a combination of series and parallel.

It should be appreciated that the present invention may be used in a variety of modes such as a static mode (where the beam flexes) and a dynamic mode (where the cantilever beam oscillates) in order to perform a variety of measurements.

For example the invention may be used in a contact mode where the sensor is scanned at a constant force between the sensor and a sample surface to obtain a 3D topographical map.

In an Intermittent Contact (Tapping Mode) the cantilever beam is oscillated at or near its resonant frequency. The oscillating tip is then scanned at a height where it barely touches or "taps" the sample surface. The analyser monitors the sensor position and a vibrational amplitude to obtain topographical and other property information allowing topographical information can be obtained even for fragile surfaces.

An advantage of the present invention is that the optical readout of the grating structure 1220 leads to increased sensitivity over existing free space optical monitoring. The present invention uses an optical resonant cavity formed between the grating structure 1220 and the cantilever beam 1210, or doubly clamped beam, coupled to a waveguide to increase an amplitude of a signal output from the sensor 1200 to levels significantly above the shot noise and thereby increasing the signal to noise ratio.

Another advantage is that the necessity to align the optics of an AFM whenever the probe is replaced is effectively eliminated due to the close coupling of the optical cavity to the waveguide. This is because the sensor 1200 and the AFM may be fabricated such that when installed, the waveguide layer 1223 aligns with the light source 1300 in the AFM.

In addition, Brownian motion noise may be reduced by clamping the beam at each end and a further reduction in Brownian noise may be made by cooling the sensor 1200.

Finally, miniaturization of the AFM may be achieved allowing multiple beams and AFM tips to form an array and to be integrated in the one structure, effectively increasing the scan rate.

Referring to FIGS. 2 and 3, although the pattern or shape of the input grating coupler 215, the interrogating grating coupler 220, or the output grating coupler 225 are shown as being grooves, it should be appreciated that the pattern or shape of the input grating coupler 215, the interrogating grating coupler 220, and the output grating coupler 225 may include other patterns or shapes.

Figure 14:
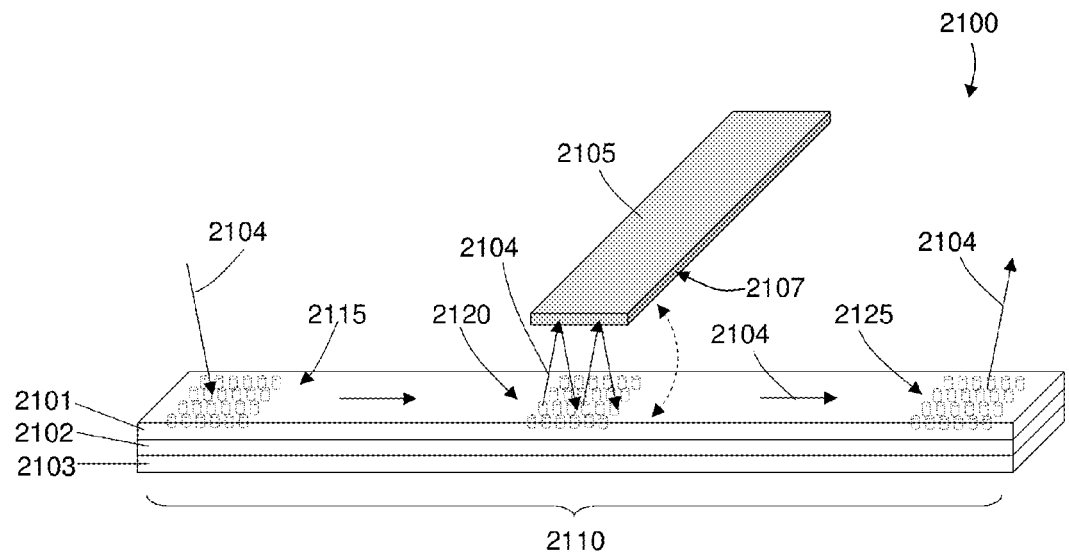
FIG. 14 shows a perspective view of an optical sensor according to a further embodiment of the present invention.

FIG. 14 shows a perspective view of an optical sensor 2100 according to a further embodiment of the present invention. Similar to FIGS. 2 and 3, the optical sensor 2100 includes a grating coupled resonating structure 2110. The grating coupled resonating structure 2110 comprises an input grating coupler 2115, an interrogating grating coupler 2120 and an output grating coupler 2125. The interrogating grating coupler 2120 is placed directly under and adjacent to the cantilever 2105 such that the interrogating grating coupler 2120 and the cantilever 2105 form a resonant cavity. In order to form a resonant cavity, the cantilever 2105 must be positioned sufficiently close to the interrogating grating coupler 2120. In some embodiments, a distance between a bottom surface of the cantilever 2105, and the top surface of the interrogating grating coupler 2120 range from less than 1 μm and 30 μm for light at infra-red wavelengths. However it should be appreciated that the distance will vary according to the wavelength of operation of the light, as would be understood by a person skilled in the art.

Generally, the distance between the cantilever 2105 and the interrogating grating coupler 2120 is less than a wavelength of the wavelength of operation to a number of wavelengths of the wavelength of operation. An amplitude of light output (or a response) from the resonant cavity varies cyclically through constructive and destructive interference as the separation changes through integer numbers of quarter wavelengths (for a round trip path length in half wavelengths).

In some embodiments, the cantilever 2105 includes a reflective surface 2107, where the reflective surface 2107 is opposite the interrogating grating coupler 2120.

Unlike the embodiment in FIG. 2 which was formed from a plurality of grooves forming a one dimensional (1D) grating coupler, in this embodiment, each of the input grating coupler 2115, the interrogating grating coupler 2120 and the output grating coupler 2125 are formed from an array of holes forming a two-dimensional (2D) grating coupler.

Figure 15:
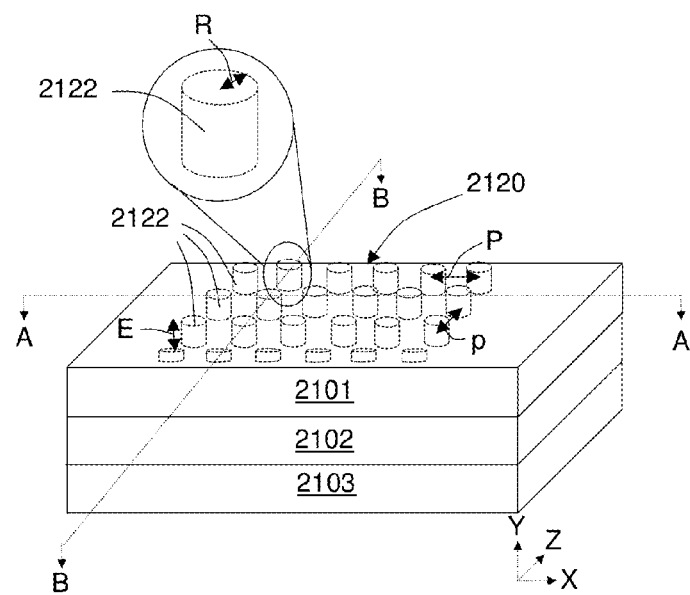
FIG. 15 shows a close-up perspective view of an interrogating grating coupler of FIG. 14, according to an embodiment of the present invention.

FIG. 15 shows a close-up perspective view of the interrogating grating coupler 2120 of FIG. 14, FIG. 16 shows a sectional view through section A-A of FIG. 15, and FIG. 17 shows a sectional view through section B-B of FIG. 15 according to an embodiment of the present invention. However it should be appreciated that the input grating coupler 2115, and the output grating coupler 2125 may be formed in a similar manner.

In some embodiments, the input grating coupler 2115, the interrogating grating coupler 2120 and the output grating coupler 2125 are etched in a Silicon on Insulator (SOI) layer 2101 using any suitable method known in the art. The SOI layer 2101 may be made from silicon, or silicon nitride however it is not limited to such materials, but it should have a higher refractive index than the layer(s) above and the layer(s) below the SOI layer 2101. In some embodiments, the SOI layer 2101 is between 50 nm and 800 nm thick. More preferably, the SOI layer 2101 is between 220 nm and 520 nm thick.

In some embodiments, the SOI layer 2101 is formed on a Buried Oxide (BOX) layer 2102, and the BOX layer 2102 is formed on a substrate 2103. In some embodiments the BOX layer is also made from silicon dioxide and is about 100 nm to 2000 nm thick. However a person skilled in the art will realise that other suitable thicknesses may be used, as can other suitable materials.

In some embodiments, the sensor 2100 may optionally include a Top Oxide (TOX) layer (not shown) formed on the SOI layer 2101, once the holes 2122 have been etched in the SOI layer 2101. The TOX layer aids the reduction of interface losses and back reflections. The TOX layer may be between 100 nm and 2000 nm thick, and made from silicon dioxide. However it should be appreciated that other thicknesses and other materials may be used.

In addition, some embodiments may include a bottom reflector (not shown) positioned between the BOX layer 2102 and the substrate 2103 to improve the coupling efficiency of the input grating coupler 2115, the interrogating grating coupler 2120 and the output grating coupler 2125 by reflecting light. However it should be appreciated that in some applications the bottom reflector is not necessary. For example in Atomic Force Microscopy applications, it might be beneficial to be able to visually see through the substrate.

The bottom reflector may be made from Aluminium. However other high reflectance materials may be used. In addition, the bottom reflector may incorporate a dielectric mirror formed by alternating high and low refractive index layers and tuned to the wavelength of operation, for example silicon dioxide may be used for the low refractive index layer (~1.45 at 1550 nm) and silicon may be used as the high refractive index layer (~3.48 at 1550 nm) or silicon nitride may be used as the high refractive index layer (~1.9 at 1550 nm). In order to form a low loss waveguide in the SOI layer 2101, the TOX layer and the BOX layer 2102 should have a lower refractive index than the SOI layer 2101 layer for a desired wavelength.

Adjacent holes 2122 in the array of holes have a pitch p in the X axis and a pitch P in the Z axis. In addition, each hole 2122 has a radius R, and is etched to an etch depth E.

Although the array is shown in FIG. 11 as being rectangular in shape, in some embodiments, the array may be square in shape. However it should be appreciated that the array may form any suitable regular or irregular shape. Further, each hole 2122 has a same etch depth E, a same radius R, a same pitch p between adjacent holes 2122, and a same pitch P between adjacent holes 2122, creating a two dimensional (2D) grating couple. However it should be appreciated that pitch p may be different to pitch P, or the holes 2122 may be randomly distributed. It should be further appreciated that the radius R of the holes 2122 may be different and that one or more holes 2122 may have different depths E.

FIG. 18 shows a side sectional view of another embodiment of a two dimensional interrogating grating coupler, according to an embodiment of the present invention. As shown in FIG. 18, holes 2222 of the interrogating grating coupler 2220 are at different etch depths E.

Although each hole 2122, 2222 in the array is shown in FIGS. 14-18 as being cylindrical, it should be appreciated that each hole 2122, 2222 may be any suitable regular or irregular shape.

As explained previously a 1D grating coupler includes a series of grooves on a surface of the SOI layer which, as shown in FIG. 3, results in a series of notches in a surface of the SOI layer when a section is taken through a single axis, namely an X axis.

In the case of a 2D grating coupler, a section taken in an X axis results in a series of notches and a section taken in a Z axis results in a series of notches.

Dimensions of the input grating coupler 2115, the interrogating grating coupler 2120 and the output grating coupler 2125 are chosen according to a chosen wavelength of operation of light from the light source. The light may be at any suitable wavelength between infra-red wavelengths (about 700 nm to 1 mm) and ultra-violet wavelengths (about 10 nm to 380 nm), including visible wavelengths (about 380 nm to 700 nm).

In particular, parameters such as the SOI layer 2101 thickness and material, the BOX layer 2102 thickness and material, the pitch P, the pitch p, the Radius R and the depth E may be tuned, for a wavelength of operation, by simulation. The process of tuning is described in more detail in a paper (Lee Carroll, Dario Gerace, Ilaria Cristiani, and Lucio C. Andreani, "Optimising polarization-diversity couplers for Si-photonics: reaching the −1 dB coupling efficiency threshold", Optical Society of America, Optics Express, Vol. 22, No. 12 (2014)) for tuning the coupling efficiency between a SOI and a fibre optic. The paper describes optimising a 2D grating structure for coupling with a fibre optic waveguide used in the telecoms industry, and provides an example for a wavelength of operation at infra-red wavelengths.

Referring to section 3 of the paper, tuning the parameters of the 2D structure of FIGS. 10-13, may be performed using a three-dimensional finite-difference time-domain (3D-FDTD) simulation on the 2D structure by experimenting with dimensions of the parameters. However a 3D-FDTD simulation can take 1000 times longer to run than a two-dimensional finite-difference time-domain (2D-FDTD) simulation. As such the 1D grating coupler is first optimised using a 2D-FDTD simulation, and some of the optimised parameters are used to perform the 3D-FDTD simulations of the 2D grating coupler. The effect of varying the parameters of a grating coupler may be investigated by computer simulation in order to optimise the grating coupler to best suit a radiation pattern from different sources, such as an optical fibre or a laser diode, or light output from the grating coupler.

Referring again to section 3 of the paper, the 2D-FDTD simulations performed on a 1D structure " . . . depend on the Si-layer [the SOI layer 2101] thickness (S), the etch-depth (E) [etch depth E], the BOX [the BOX layer 2102] thickness (B), the hole-radius (R) [radius R], and the grating-pitch (P) [pitch P and/or pitch p] of the SOI-PDC design [the input grating coupler 2115, the interrogating grating coupler 2120 or the output grating coupler 2125]. Imposing the boundary conditions of λP=1550 nm [the wavelength of operation], and θ=10° [an angle of incidence of the light on the input grating coupler 2115, the interrogating grating coupler 2120 or the output grating coupler 2125], reduces the number of independent design parameters to four—(i) the Si-layer thickness [the SOI layer 2101], (ii) the BOX [the BOX layer 2102] thickness, (iii) the normalized etch-depth (E/S) [the etch depth E divided by the thickness of the SOI layer 2101], and (iv) the normalized hole-size (R/P) [radius R divided by the pitch P or pitch p]. . . . The parameter-space around these starting values is explored by generating ≈25 unique SOI-PDC [2D structure] designs, each using the initial estimate of the Si-layer and BOX thickness, but spanned by different combinations of E/S and R/P values. The coupling efficiency of each design is calculated using 3D-FDTD, with the grating-pitch iteratively adjusted until λP of CET(φ=45°) converges to 1550±2 nm. A contour plot of CET(φ=45°) spanned by E/S and R/P can then be built-up, from which the optimum combination of E/S and R/P (for the initial estimates of Si-layer and BOX thickness) can be immediately identified. Next, a small sweep of the BOX thickness around the initial estimate is performed for the SOI-PDC designs with the optimum pair of E/S and R/P values. This identifies the optimized design parameters (E, R, P, and B) of the SOI-PDC with the initial estimate of the Si-layer thickness. When this procedure is repeated for different Si-layer thicknesses around the initial estimated value, i.e. when the design parameter of S is also allowed to vary, then the globally optimized set of all parameters can be identified.

"Each design has a unique combination of Si-layer thickness (from S=160 nm to 520 nm, in 19 steps) [the SOI layer 2101], BOX-thickness (from B=1800 nm to 2100 nm, in 7 steps) [the BOX layer 2102], etch-depth (from E=0.2×S to 0.8×S, in 7 steps), and duty-cycle cycle [duty-cycle (DC) of a 1D grating structure which is a ratio between a width of a groove to a period of the grooves, as would be understood by a person skilled in the art] (from DC=0.2 to 0.8, in 7 steps). Each design is individually centred on λP=1550±2 nm [the wavelength of operation] by tuning the grating-pitch [pitch P and pitch p]. The hierarchy of the parameter sweep is S-B-E-DC, so while the duty-cycle changes for each design, the Si-layer thickness only changes every 343 designs (343=7×7×7), etc." The simulations of FIG. 3(a) identified that the best performing structure has a SOI layer 2101 thickness of 420 nm, a BOX layer 2102 thickness of 1900 nm, an etch depth E of 252 nm, and DC=0.7) at a wavelength of operation of 1550 nm.

Referring again to section 4.1 of the paper, "The design parameters of the best performing SOI 1D-GC design . . . are used as the starting values for the optimization of the high performance SOI-PDC design. After following the procedure outlined in Section 3, the optimized SOI-PDC design parameters are identified as S=400 nm, B=1900 nm, E/S=291 nm/400 nm=0.73, and R/P=167 nm/584 nm=0.29. As shown in the contour plot of FIG. 3(b), this SOI-PDC design offers a coupling efficiency of −1.9 dB (65%), meaning that the performance gap with respect to the best SOI 1D-GC is just 0.5 dB. The coupling spectrum of this optimized SOI-PDC design is given in FIG. 2(b), and has a 1 dB bandwidth of 38 nm, which is adequate for multiplexed telecom applications. To establish if the performance gap can be closed for all Si-layer thicknesses, 3D-FDTD optimization was also carried-out for SOI-PDCs with S=220 nm, 320 nm, and 520 nm.

As a result, the paper found the optimal design of 2D structure without a reflector at a wavelength of 1550 nm to have a SOI layer 2101 thickness of 400 nm, an etch depth E of 291 nm, a hole 1022 radius R of 167 nm, a pitch P=pitch p of 584 nm, and a BOX layer 2102 thickness of 1900 nm. However it should be appreciated that the dimensions of the structure will vary according to many variables including the BOX layer 2102, and the wavelength of operation.

As previously mentioned, a reflector may be positioned between the BOX layer 2102 and the substrate 2103 to improve the coupling efficiency of the input grating coupler 2115, the interrogating grating coupler 2120 and the output grating coupler 2125, which generally improves the coupling efficiency by 1 dB. Referring to section 4.2 of the paper, "FIG. 4(a) shows the coupling efficiency of 4704 unique SOI 1D-GC designs with bottom-reflector, as calculated by 2D-FDTD simulations. Each design has a unique combination of Si-layer thickness (from S=150 nm to 290 nm, in 8 steps), BOX-thickness (from B=1550 nm to 2100 nm, in 12 steps), etch-depth (from E=0.2×S to 0.8×S, in 7 steps), and duty-cycle (from DC=0.2 to 0.8, in 7 steps). The range of the BOX thicknesses in this sweep spans 550 nm (≈1550 nm/2nOX) to ensure the identification of a condition for perfectly constructive interference. As was the case in Section 4.1, each 1D-GC design is individually tuned to λP=1550±2 nm, and the sweep hierarchy is S-B-E-D, so that the Si layer thickness changes only once every 588 designs (588=12×7×7). The sweep identifies the best-performing uniform SOI 1D-GC with bottom-reflector as having a coupling efficiency of −0.6 dB (87%) with S=170 nm, B=1600 nm (or 2150 nm), E=51 nm, DC=0.5, and P=694 nm. This is the highest reported calculated coupling-efficiency for a uniform SOI 1D-GC design with bottom-reflector. However, it is somewhat less than the reported coupling efficiency from calculations of apodized SOI 1D-GC designs with bottom-reflector (−0.45 dB=92%) [9].

Both of these calculations compare well with reports of measured coupling efficiencies of −0.62 dB (87%) from apodized SOI 1D-GCs with bottom-reflectors.

"Using the same optimization procedure as that outlined in the previous section [for the embodiment without a reflector], the parameters for the optimized SOI-PDC design with bottom-reflector are identified as S=160 nm, B=2175 nm, E/S=80 nm/160 nm=0.5, and R/P=209 nm/696 nm=0.3. As shown in the contour plot of FIG. 4(b), this SOI-PDC design offers a coupling efficiency of −0.95 dB (80%). The coupling spectrum of this optimized SOI-PDC with bottom-reflector is given in FIG. 2(c), and has a 1 dB bandwidth of 42 nm."

As a result, the paper found the optimal design of a 2D structure with a reflector at a wavelength of 1550 nm to have a SOI layer 2101 thickness of 160 nm, an etch depth E of 80 nm, a hole 2122 radius R of nm, a pitch P=pitch p of 696 nm, and a BOX layer 2102 thickness of 2175 nm. However it should be appreciated that the dimensions of the structure will vary according to many parameters including the BOX layer 2102, and the wavelength of operation of a light source.

Referring back to FIG. 14, in use, a light source (not shown) is connected to the input grating coupler 2115 using a waveguide or optical fibre for example. Similarly, the output grating coupler 2125 is connected to an analyser (not shown), via a waveguide or optical fibre for example, for analysing light output from the grating coupled resonating structure 2110. The light output from the grating coupled resonating structure 2110 may be analysed in real time or stored on the analyser or a computing device for example, for analysis at a later time. Although the light is shown as being coupled via the input grating coupler 2115 it should be appreciated that the light may be coupled using any suitable method. Similarly, although the light is shown as being output via the output grating coupler 2125, it should appreciated that the light may be coupled to the analyser via any suitable method.

In some embodiments, a reflective surface, similar to the reflective surface 2107, may be placed above the input grating coupler 2115 and above the output grating coupler 2125. In this embodiment, light is coupled into the sensor 2100 from under the input grating coupler 2115 and light is coupled out of the sensor 2100 from under the output grating coupler 2125. In this case the substrate 2103 is substantially transparent to the wavelength of operation to allow light to penetrate through the substrate 2103 and the BOX layer 2102 and into the SOI layer 2101. In another embodiment, there may be no output grating coupler 2125, and light may be coupled to a photodetector coupled directly to the SOI layer 2101.

Solid arrows 2104 illustrate a path of light through the optical sensor 2100. Similar to the embodiment shown in FIGS. 2, 3, 10 and 11, light is input to the input grating coupler 2105. The light then propagates in the SOI layer 2101, to the interrogating grating coupler 2120. Light exits the interrogating grating coupler 2120 in a near perpendicular direction towards the cantilever 2105, and is reflected back by the cantilever 2105 allowing the light to resonate between the cantilever 2105 and the interrogating grating coupler 2120. Light modulated by the resonant cavity then propagates along the grating coupled resonating structure 2110 in the SOI layer 2101 to the analyser via the output grating coupler 2125.

The analyser analyses an amount, modulation and/or a frequency of light coupled to the output grating coupler 2125, which is a function of the distance between the interrogating grating coupler 2120 and the cantilever 2105, in order to determine a separation between the interrogating grating coupler 2120 and the cantilever 2105.

As explained previously a 1D grating coupler includes a series of grooves. The grooves are etched in a surface of the SOI layer 2101 which results in a series of notches in a surface of the SOI layer when a section is taken through a single axis. The notches that result may be similar to FIG. 16.

In the case of a 2D grating coupler, a section taken in an X axis of FIG. 15 results in a series of notches in a surface of the SOI layer 2101 as shown in FIG. 16. Similarly, a section taken in a Z axis of FIG. 15 results in a series of notches in a surface of the SOI layer 101 as shown in FIG. 17.

Although the interrogating grating coupler 2120 may be used with a single cantilever, it should be appreciated that the interrogating grating coupler 2120 or the interrogating grating coupler 1420 may be used as an alternative to the interrogating grating coupler used in multiple cantilever designs of FIG. 4, 6, 7, 8 or 9.

An advantage, of using the 2D grating coupler of FIGS. 15-18 for the input grating coupler 2115 and the output grating coupler 2125 over the 1D grating coupler of FIGS. 2, 3, 10 and 11, is that the coupling efficiency of 1D grating coupler depends on the polarisation of the fibre optic cable, and can be unknown in telecom fibre optic cables. However this problem may be overcome by 2D grating couplers.

Although the invention has been described in relation to a cantilever or microcantilever, thus is fixed at a single end, it should be appreciated that the present invention may be applied to flexible beams fixed at opposing ends, a membrane or any suitable MicroElectroMechanical Systems (MEMS) structure positioned above the interrogating grating coupler. In the case of a beam, the interrogating grating coupler is positioned between the opposing ends of the beam.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

Limitations in the patent claims should be interpreted broadly based on the language used in the claims, and such limitations should not be limited to specific examples described herein. In this specification, the terminology "present invention" is used as a reference to one or more aspects within the present disclosure. The terminology "present invention" should not be improperly interpreted as an identification of critical elements, should not be improperly interpreted as applying to all aspects and embodiments, and should not be improperly interpreted as limiting the scope of any patent claims.

What is claimed is:

1. An optical sensor including:
   a MicroElectroMechanical Systems (MEMS) structure; and a grating coupled resonating structure positioned adjacent to the MEMS structure, the grating coupled resonating structure comprising:
  an input grating coupler for inputting light into the optical sensor;
  an output grating coupler for outputting light from the optical sensor; and
  an interrogating grating coupler configured to direct light towards the MEMS structure and collect light reflected by the MEMS structure; wherein
the input grating coupler and the output grating coupler are spaced a distance from the interrogating grating coupler;
the interrogating grating coupler has a plurality of holes in a two dimensional array forming a two dimensional grating; and
the interrogating grating coupler and the MEMS structure form an optical resonant cavity.

2. The sensor of claim 1 wherein the MEMS structure is a cantilever.

3. The sensor of claim 1 wherein the array is a regular shape.

4. The sensor of claim 3 wherein the array forms a square.

5. The sensor of claim 3 wherein the array forms a rectangle.

6. The sensor of claim 1 wherein the array is an irregular shape.

7. The sensor of claim 1 wherein the holes are etched in a Silicon on Insulator (SOI) layer.

8. The sensor of claim 7 wherein the SOI layer is formed on a Buried Oxide (BOX) layer.

9. The sensor of claim 8 wherein the BOX layer is formed on a substrate.

10. The sensor of claim 8 wherein a waveguide layer is formed on the BOX layer.

11. The sensor of claim 1 wherein each hole is cylindrical in shape.

12. The sensor of claim 1 wherein the input grating coupler is one dimensional.

13. The sensor of claim 1 wherein the input grating coupler includes a plurality of holes forming an array.

14. The sensor of claim 1 wherein the output grating coupler is one dimensional.

15. The sensor of claim 1 wherein the output grating coupler is two dimensional.

16. The sensor of claim 1 wherein the output grating coupler includes a plurality of holes forming an array.

17. A method of detecting a deflection of a MEMS structure, the method comprising the steps of:
  inputting an optical signal into an input grating coupler;
  inputting the optical signal from the input grating coupler into an interrogating grating coupler, the interrogating grating coupler being arranged to form an optical resonant cavity with the MEMS structure;
  inputting the optical signal from the interrogating grating coupler to an output grating coupler, wherein the input granting coupler and the output granting coupler are spaced a distance from the interrogating granting coupler; and
  analyzing the optical signal output from the interrogating grating coupler to determine a deflection of the MEMS structure; wherein
  the interrogating grating coupler includes a plurality of holes in a two-dimensional array.

18. The method of claim 17 wherein the MEMS structure is a cantilever beam.

19. The method of claim 17 wherein the input grating coupler is two dimensional.

20. The method of claim 17 wherein the output grating coupler is two dimensional.

* * * * *